(12) United States Patent
Ishitsuka

(10) Patent No.: US 12,710,522 B2
(45) Date of Patent: Aug. 18, 2026

(54) APPARATUS

(71) Applicant: CANON MEDICAL SYSTEMS CORPORATION, Otawara (JP)

(72) Inventor: Masaaki Ishitsuka, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 230 days.

(21) Appl. No.: 16/925,435

(22) Filed: Jul. 10, 2020

(65) Prior Publication Data

US 2021/0018605 A1 Jan. 21, 2021

(30) Foreign Application Priority Data

Jul. 18, 2019 (JP) ................................ 2019-132510

(51) Int. Cl.
*G01S 7/52* (2006.01)
*A61B 8/00* (2006.01)

(52) U.S. Cl.
CPC ........ *G01S 7/52025* (2013.01); *A61B 8/5246* (2013.01); *A61B 8/5269* (2013.01); *A61B 8/54* (2013.01); *G01S 7/5202* (2013.01)

(58) Field of Classification Search
None
See application file for complete search history.

(56) References Cited

U.S. PATENT DOCUMENTS 6,500,120 B1 * 12/2002 Anthony ............. G01S 15/8915 600/443
8,177,718 B2 * 5/2012 Savord .................. G01S 7/5208 600/447
2003/0231125 A1 * 12/2003 Freeman ............ G01S 7/52095 341/143
2005/0148874 A1 * 7/2005 Brock-Fisher ...... G01S 15/8925 600/447

(Continued)

FOREIGN PATENT DOCUMENTS

EP 3 111 849 A1 1/2017
GB 2142142 A * 1/1985 .............. A61B 8/06

(Continued)

OTHER PUBLICATIONS

Kim, Minkyoung, et al. "Design of a reconfigurable phase controller for focused ultrasound therapeutic device." 2014 IEEE International Ultrasonics Symposium. IEEE, 2014. (Year: 2014).*

(Continued)

*Primary Examiner* — Jonathan D Armstrong
(74) *Attorney, Agent, or Firm* — Oblon, McClelland, Maier & Neustadt, L.L.P.

(57) ABSTRACT

An apparatus according to the embodiment includes a first delay circuit, a second delay circuit, and processing circuitry. The first delay circuit delays an ultrasound signal in a first channel using a plurality of capacitors. The second delay circuit delays an ultrasound signal in a second channel using a plurality of capacitors. The processing circuitry make a first write start position in which writing the ultra- (Continued)

sound signal in the capacitor in the first delay circuit is started and a second write start position in which writing the ultrasound signal in the capacitor in the second delay circuit is started different from each other.

13 Claims, 18 Drawing Sheets

(56) References Cited

U.S. PATENT DOCUMENTS

| | | | | |
|---|---|---|---|---|
| 2009/0171213 | A1* | 7/2009 | Savord | G01S 7/5208 600/447 |
| 2013/0107671 | A1* | 5/2013 | Amemiya | G01S 7/52026 367/135 |
| 2016/0363657 | A1 | 12/2016 | Nakagawa et al. | |
| 2018/0214123 | A1 | 8/2018 | Takano | |
| 2019/0008477 | A1 | 1/2019 | Ishitsuka | |

FOREIGN PATENT DOCUMENTS

| | | | | |
|---|---|---|---|---|
| JP | 2019-208939 | A | 12/2019 | |
| WO | WO-2007099473 | A1 * | 9/2007 | G01S 15/8909 |
| WO | WO-2007099474 | A1 * | 9/2007 | G01S 15/8927 |
| WO | WO-2010021709 | A1 * | 2/2010 | G01N 29/0654 |
| WO | WO 2017/026019 | A1 | 2/2017 | |
| WO | WO 2017/026278 | A1 | 2/2017 | |
| WO | WO-2017047329 | A1 * | 3/2017 | G01S 15/8915 |
| WO | WO-2019232358 | A9 * | 4/2020 | A61B 18/1477 |
| WO | WO-2020068473 | A1 * | 4/2020 | A61B 5/0095 |
| WO | WO-2021201380 | A1 * | 10/2021 | |

OTHER PUBLICATIONS

Extended European Search Report issued Dec. 14, 2020 in European Patent Application No. 20185004.7, 9 pages.

Extended European Search Report issued Dec. 14, 2020 in European Patent Application No. 15190796.1, 9 pages.

Office Action mailed Feb. 7, 2023, in corresponding Japanese Patent Application No. 2019-132510, 3 pages.

* cited by examiner

FIG.2

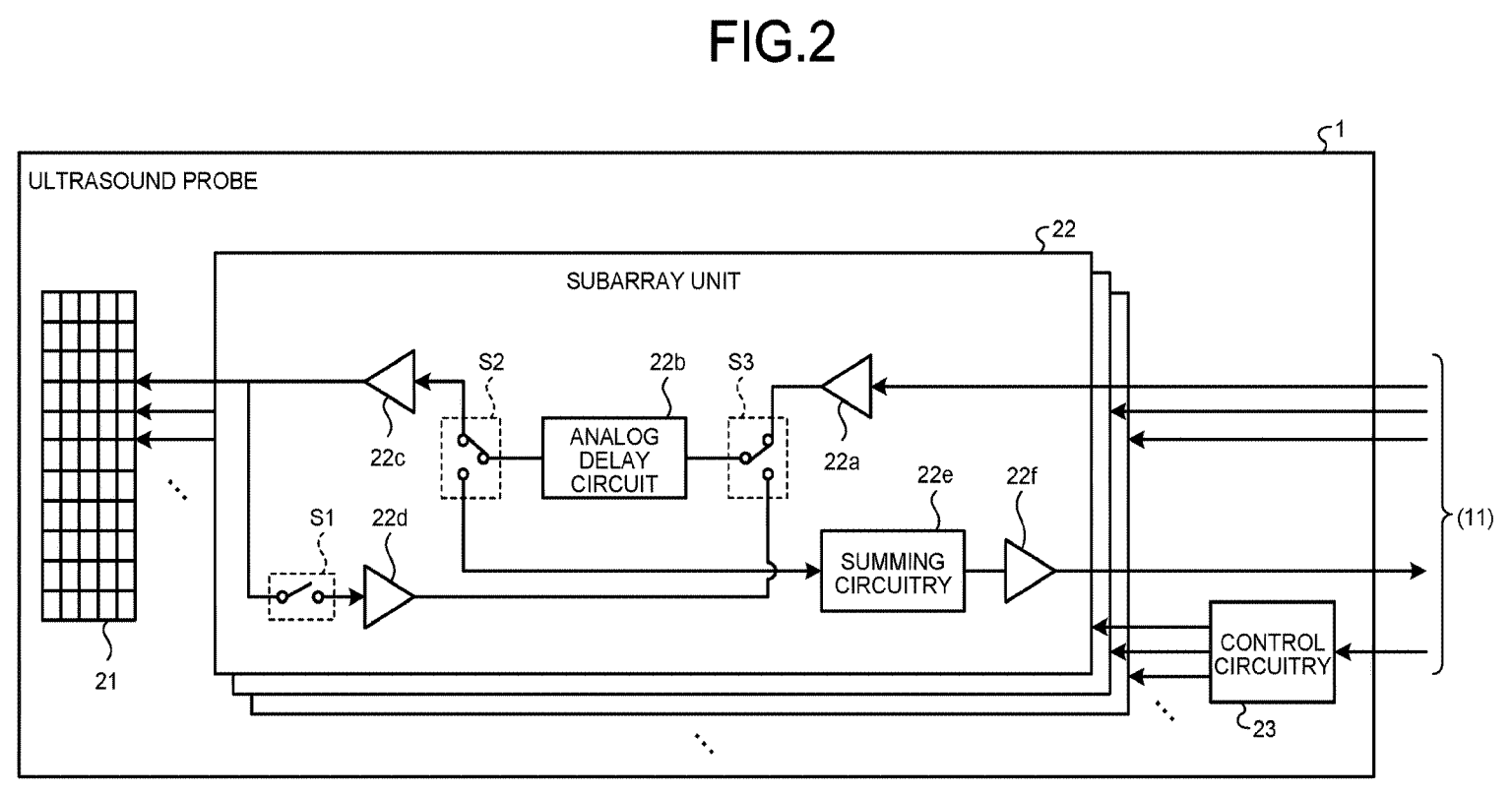

(11)
1
CONTROL CIRCUITRY
23
22
22f
22e
SUMMING CIRCUITRY
22a
S3
SUBARRAY UNIT
22b
ANALOG DELAY CIRCUIT
S2
22c
22d
S1
ULTRASOUND PROBE
21

FIG.4

APPARATUS

CROSS-REFERENCE TO RELATED APPLICATIONS

This application is based upon and claims the benefit of priority from Japanese Patent Application No. 2019-132510, filed on Jul. 18, 2019; the entire contents of which are incorporated herein by reference.

FIELD

An embodiment relates to an apparatus.

BACKGROUND

There is an ultrasound diagnostic apparatus that generates ultrasound image data representing an ultrasound image obtained by imaging an internal condition of a subject with an ultrasound probe including a delay circuit (analog delay circuit) that performs delay processing on a reflected-wave signal using an analog system.

BRIEF DESCRIPTION OF THE DRAWINGS

FIG. 2 is a diagram for describing an example of the configuration of an ultrasound probe according to the embodiment;

FIG. 4 is a diagram representing an example of a plurality of write control signals and a plurality of read control signals;

DETAILED DESCRIPTION

An apparatus according to the embodiment includes a first delay circuit, a second delay circuit, and processing circuitry. The first delay circuit delays an ultrasound signal in a first channel using a plurality of capacitors. The second delay circuit delays an ultrasound signal in a second channel using a plurality of capacitors. The processing circuitry make a first write start position in which writing the ultrasound signal in the capacitor in the first delay circuit is started and a second write start position in which writing the ultrasound signal in the capacitor in the second delay circuit is started different from each other.

An embodiment of an ultrasound probe and an ultrasound diagnostic apparatus and each modification will be described in detail below with reference to the accompanying drawings.

EMBODIMENT

Figure 1:
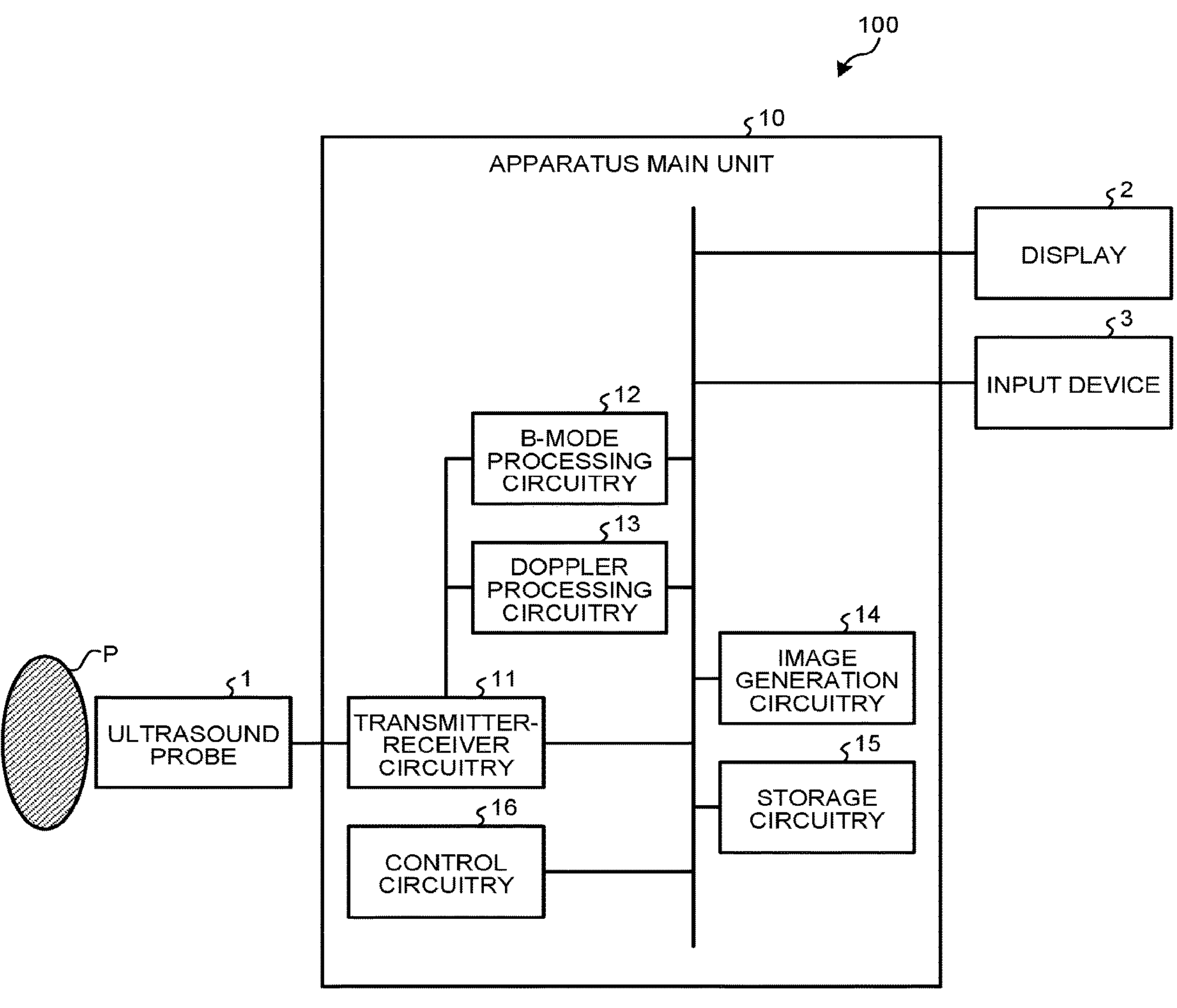
FIG. 1 is a diagram for describing an example of the configuration of an ultrasound diagnostic apparatus according to an embodiment.

First of all, an example of the configuration of an ultrasound diagnostic apparatus to which an ultrasound probe is applied according to the embodiment will be described. FIG. 1 is a diagram for describing an example of a configuration of an ultrasound diagnostic apparatus 100 according to the embodiment. As illustrated in FIG. 1, the ultrasound diagnostic apparatus 100 according to the embodiment includes an ultrasound probe 1, a display 2, an input device 3, and an apparatus main unit 10. The ultrasound diagnostic apparatus 100 is an example of an apparatus.

The ultrasound probe 1 is detachably connected to the apparatus main unit 10. When ultrasound is transmitted from the ultrasound probe 1 to a subject P, the transmitted ultrasound is reflected sequentially on a surface with acoustic impedance discontinuity. The reflected ultrasound is received by the ultrasound probe 1 as reflected waves (echoes). The reflected waves are converted into reflected-wave signals in the ultrasound probe 1. The amplitude of the reflected-wave signals depends on the difference in acoustic impedance on the discontinuity surface on which ultrasound is reflected. Reflected-wave signals in the case where transmitted ultrasound pulses are reflected on a moving blood flow, a heart wall, or the like, undergo a frequency shift because of the Doppler effect depending on velocity components of a mobile object with respect to the direction in which ultrasound is transmitted. The reflected-wave signals are then converted into a summing signal to be described below in the ultrasound probe 1 and the summing signal is then output. The ultrasound probe 1 may be of a convex type or a sector type, and various types of ultrasound probes are usable as the ultrasound probe 1.

The ultrasound probe 1 includes a plurality of transducers 21 (refer to FIG. 2) to be described below. The transducers 21 are arranged two-dimensionally in a lateral direction and an elevation direction and are divided into multiple subarrays. The subarrays, for example, refer to respective groups into each of which a given number of transducers 21 are grouped. One subarray includes the given number of transducers 21. The ultrasound probe 1 is an example of the apparatus. A configuration of the ultrasound probe 1 will be described below.

The display 2 displays a graphical user interface (GUI) for a user of the ultrasound diagnostic apparatus 100 to input various types of setting requests using the input device 3 and displays an ultrasound image that is represented by ultrasound image data that is generated in the apparatus main unit 10, etc. The display 2 is an example of a display unit.

The input device 3 is implemented using a track ball, a switch, a dial, a touch command screen, a footswitch, a joystick, or the like. The input device 3 receives the various setting requests from the user of the ultrasound diagnostic apparatus 100 and transfers the received various setting requests to the apparatus main unit 10. For example, the input device 3 receives various setting requests for controlling the ultrasound probe 1 and transfers the various setting requests to the apparatus main unit 10.

The apparatus main unit 10 controls transmission of ultrasound performed by the ultrasound probe 1 and reception of reflected waves performed by the ultrasound probe 1. The apparatus main unit 10 generates an ultrasound image based on the summing signal that is transmitted from the ultrasound probe 1 and to be described below. As illustrated in FIG. 1, the apparatus main unit 10 includes transmitter-receiver circuitry 11, B-mode processing circuitry 12, Doppler processing circuitry 13, image generation circuitry 14, storage circuitry 15, and control circuitry 16.

Under the control of the control circuitry 16, the transmitter-receiver circuitry 11 transmits and receives various types of data, etc., to and from the ultrasound probe 1 and the apparatus main unit 10. For example, the transmitter-receiver circuitry 11 repeatedly generates a transmission pulse (rate pulse) for forming transmission ultrasound at a given rate frequency (pulse repetition frequency (PRF)) and transmits the generated transmission pulses to the ultrasound probe 1.

For example, the transmitter-receiver circuitry 11 transmits, to the ultrasound probe 1, a delay (transmission delay) to ultrasound that is transmitted from the ultrasound probe 1. Specifically, the transmitter-receiver circuitry 11 transmits a transmission delay to ultrasound that is output (transmitted) by each transducer 21.

The transmitter-receiver circuitry 11 transmits, to the ultrasound probe 1, a delay (a reception delay) to a reflected-wave signal. Specifically, the transmitter-receiver circuitry 11 transmits, to the ultrasound probe 1, a reception delay to a reflected-wave signal that is transmitted by each transducer 21.

The transmitter-receiver circuitry 11 includes an A/D (Analog to Digital) converter and a receiving beamformer. When the transmitter-receiver circuitry 11 receives an analog summing signal of each subarray that is output from the ultrasound probe 1, first of all, the A/D converter converts the analog summing signal into a digital summing signal. The receiving beamformer performs a phasing and summing processing on the digital summing signal of each subarray, thereby generates reflected-wave data. The receiving beamformer transmits the generated reflected-wave data to the B-mode processing circuitry 12 and the Doppler processing circuitry 13.

The B-mode processing circuitry 12 receives the reflected-wave data that is output from the transmitter-receiver circuitry 11. The B-mode processing circuitry 12 performs logarithmic amplification, envelope detection, etc., on the received reflected-wave data, thereby generating data (B-mode data) in which the signal intensity is expressed by the intensity of illuminance. The B-mode processing circuitry 12 is, for example, implemented using a processor.

The Doppler processing circuitry 13 receives the reflected-wave data that is output from the transmitter-receiver circuitry 11. The Doppler processing circuitry 13 then performs frequency analysis on rate information from the received reflected-wave data, extracts blood flows, tissue and contrast agent echo components resulting from the Doppler effect, and generates data (Doppler data) obtained by extracting mobile object information, such as an average rate, dispersion, power, etc., with respect to a large number of points. The Doppler processing circuitry 13, for example, is implemented using the processor.

The image generation circuitry 14 generates ultrasound image data from the sets of data that are generated by the B-mode processing circuitry 12 ad the Doppler processing circuitry 13. In other words, the image generation circuitry 14 generates B-mode image data in which the echo intensity is represented by the luminance from the B-mode data that is generated by the B-mode processing circuitry 12. From the Doppler data that is generated by the Doppler processing circuitry 13, the image generation circuitry 14 generates color Doppler image data serving as an average rate image, a dispersion image or a power image representing the mobile object information or an image of a combination of the images. The image generation circuitry 14 is implemented using, for example, the processor.

The storage circuitry 15 is implemented using, for example, a random access memory (RAM), a semiconductor memory device, such as a flash memory, a hard disk, or an optical disk. For example, the storage circuitry 15 stores ultrasound image data that is generated by the image generation circuitry 14. The storage circuitry 15 may store the data that is generated by the B-mode processing circuitry 12 and the Doppler processing circuitry 13.

The storage circuitry 15 stores various types of data, such as control programs for performing ultrasound transmission and reception, image processing and display processing, diagnostic information (for example, patient IDs and observations of a doctor), a diagnostic protocol and various types of body marks.

The storage circuitry 15 stores elements for calculating the above-described various delays (transmission delays and reception delays). For example, sets of coordinates each representing the position of each of the transducers 21 a and sets of coordinates each representing the position of focal point are taken as such elements.

The control circuitry 16 controls the whole process performed by the ultrasound diagnostic apparatus 100. For example, according to the various setting requests that are input by an operator via the input device 3 and various control programs and various types of data that are read from the storage circuitry 15, the control circuitry 16 controls the processing performed by the transmitter-receiver circuitry 11, the B-mode processing circuitry 12, the Doppler processing circuitry 13 and the image generation circuitry 14.

The control circuitry 16 controls the display 2 such that the display 2 displays the ultrasound image data that is stored in the storage circuitry 15 and the various types of image data that are stored in the storage circuitry 15, a GUI for performing the processing by the image generation circuitry 14 and the result of processing performed by the image generation circuitry 14, or the like. In the embodiment, the control circuitry 16 controls the display 2 such that the display 2 displays the ultrasound image that is represented by the ultrasound image data obtained from the summing signal to be described below. In other words, the control circuitry 16 controls the display 2 such that the display 2 displays the ultrasound image based on the summing signal. The control circuitry 16 is an example of a display controller or a display control unit.

The control circuitry 16 controls the transmitter-receiver circuitry 11 such that the transmitter-receiver circuitry 11 transmits the transmission delay for each channel and the reception delay of each channel to the ultrasound probe 1. In the embodiment, one channel is assigned to one transducer 21.

The control circuitry 16 reads, from the storage circuitry 15, the elements for calculating the various delays that are stored in the storage circuitry 15 and, based on the read elements, calculates the above-described various delays of the respective transducers 21, that is, the respective channels. The control circuitry 16 controls the transmitter-receiver circuitry 11 such that the transmitter-receiver circuitry 11 transmits the various delays of the respective channels to the ultrasound probe 1. The control circuitry 16 is implemented using, for example, the processor.

With reference to FIG. 2, an example of the configuration of the ultrasound probe 1 according to the embodiment will be described. FIG. 2 is a diagram for describing the example of the configuration of the ultrasound probe 1 according to the embodiment.

As illustrated in FIG. 2, the ultrasound probe 1 includes the transducers 21, a plurality of subarray units 22, and control circuitry 23. The apparatus main unit 10 may include the subarray units 22 and the control circuitry 23. The apparatus main unit 10 may include only the control circuitry 23 among the subarray units 22 and the control circuitry 23.

As described above, the transducers 21 are arranged two-dimensionally in the lateral direction and the elevation direction and are divided into the multiple subarrays. In the embodiment, the control circuitry 23 sets transmission delays of the respective transducers 21 and each of the transducers 21 transmits ultrasound based on a drive signal at the timing corresponding to the corresponding transmission delay to the subject P.

One subarray unit 22 is arranged for one subarray. Each of the subarray units 22 includes a buffer 22*a*, an analog delay circuit 22*b*, a pulser 22*c*, a preamplifier 22*d*, summing circuitry 22*e*, a buffer 22*f*, and switches S1, S2 and S3. Among them, the buffers 22*a*, the analog delay circuits 22*b*, the pulsers 22*c*, the preamplifiers 22*d*, and the switches S1, S2 and S3 corresponding in number to the channels forming the subarray are present in each of the subarray units 22. As described above, the buffer 22*a*, the analog delay circuit 22*b*, the pulser 22*c*, the preamplifier 22*d*, and the switches S1, S2 and S3 are arranged for each channel. In other words, the buffer 22*a*, the analog delay circuit 22*b*, the pulser 22*c*, the preamplifier 22*d*, and the switches S1, S2 and S3 are arranged for each of the transducers 21.

On the other hand, one summing circuitry 22*e* and one buffer 22*f* are arranged in each subarray unit 22. In other words, one summing circuitry 22*e* and one buffer 22*f* are arranged in one subarray.

One control circuitry 23 is arranged in the ultrasound probe 1.

The buffer 22*a*, the analog delay circuit 22*b*, the pulser 22*c*, the preamplifier 22*d*, the summing circuitry 22*e*, the buffer 22*f*, and the switches S1, S2 and S3 are arranged on at least one application specific integrated circuit (ASIC) that the ultrasound probe 1 includes and that is not illustrated in the drawings.

The buffer 22*a* is connected to the transmitter-receiver circuitry 11 and the switch S3. The transmitter-receiver circuitry 11 transmits transmission pulses to the analog delay circuits 22*b*_via the buffer 22*a*.

The analog delay circuit 22*b* is implemented using an analog circuit. The analog delay circuit 22*b* is connected to the switch S2 and the switch S3. The analog delay circuit 22*b*_includes a plurality of switched capacitors. The switched capacitor, for example, has a function of a memory device and temporarily stores an ultrasound signal. The ultrasound signal that is input to the switched capacitors is, for example, a transmission pulse that is transmitted from the transmitter-receiver circuitry 11 of the apparatus main unit 10 or a reflected-wave signal that is transmitted from the preamplifier 22*d*.

The analog delay circuit 22*b*_executes the delay processing to delay the ultrasound signal using the switched capacitors. In other words, the analog delay circuit 22*b* assigns delays to the ultrasound signal using the switched capacitors.

For example, the analog delay circuit 22*b*_executes delay processing of assigning a delay for each transducer 21 (channel) necessary to focus the ultrasound that is generated from the transducer 21 into a beam and determine transmission directivity to a transmission pulse that is supplied from the apparatus main unit 10. For example, under the control of the control circuitry 23, the analog delay circuit 22*b* assigns a delay that is set for each channel to a transmission pulse for each channel that is output from the apparatus main unit 10. The analog delay circuit 22*b* transmits the transmission pulse assigned with the delay to the pulser 22*c* via the switch S2.

Under the control of the control circuitry 23, the analog delay circuit 22*b*_executes delay processing of assigning a delay necessary to determine reception directivity to a reflected-wave signal that is transmitted from the preamplifier 22*d*. The analog delay circuit 22*b* transmits the reflected-wave signal assigned with the delay to the summing circuitry 22*e* via the switch S2. The analog delay circuit is an example of a delay circuit.

The pulser 22*c* is connected to the switch S2 and is connected to the transducer 21. Under the control of the control circuitry 23, the pulser 22*c* generates a drive signal of a given amplitude. For example, the pulser 22*c* generates a drive signal based on a transmission pulse that is transmitted from the analog delay circuit 22*b*_and transmits the generated drive signal to the transducer 21.

The preamplifier 22*d* is connected to the switch S1 and the switch S3. On receiving a reflected-wave signal that is transmitted from the transducer 21 via the switch S1, the preamplifier 22*d* amplifies the received reflected-wave signal by a gain that is set previously. The preamplifier 22*d* transmits the amplified reflected-wave signal to the analog delay circuit 22*b*_via the switch S3.

The summing circuitry **22*e* is connected to the switch S2 and the buffer 22*f*. The summing circuitry 22*e* executes a summing process of summing a plurality of reflected-wave signals on which the delay processing has been performed and that are transmitted from the analog delay circuits 22*b* corresponding respectively to a plurality of channels forming one subarray. The summing circuitry 22*e* transmits one signal (summing signal) obtained by summing the reflected-wave signals by performing the summing processing to the transmitter-receiver circuitry 11. The summing circuitry 22*e*** is an example of a summing unit. The summing signal is an example of an ultrasound signal.

The buffer **22*f* outputs the summing signal that is transmitted from the summing circuitry 22*e* to the transmitter-receiver circuitry 11. The summing circuitry 22*e* transmits the summing signal to the transmitter-receiver circuitry 11 via the buffer 22*f***.

Under the control of the control circuitry 23, when ultrasound is transmitted, the switch S1 is turned off to prevent a signal with a wide amplitude that is generated by the pulser **22*c* from being input to the preamplifier 22*d***.

When a reflected-wave signal that is transmitted from the transducer 21 is supplied to the preamplifier **22*d*, the switch S1 is turned on. In other words, when reflected waves are received, the switch S1 connects the transducer 21 and the preamplifier 22*d***.

Under the control of the control circuitry 23, the switch S2 selectively switches the destination to which an ultrasound signal that is transmitted from the analog delay circuit **22*b* is transmitted to any one of the pulser 22*c* and the summing circuitry 22*e*. For example, when ultrasound is transmitted, the switch S2 switches a destination to which a transmission pulse assigned with a delay is transmitted to the pulser 22*c*. In other words, when ultrasound is transmitted, the switch S2 connects the analog delay circuit 22*b*_and the pulser 22*c*. When reflected waves are received, the switch S2 switches a destination to which a reflected-wave signal assigned with a delay is transmitted to the summing circuitry 22*e*. In other words, when reflected waves are received, the switch S2 connects the analog delay circuit 22*b*_and the summing circuitry 22*e***.

Under the control of the control circuitry 23, the switch S3 selectively switches a source from which an ultrasound signal to be input to the analog delay circuit **22*b* is transmitted to any one of the buffer 22*a* and the preamplifier 22*d*. For example, when ultrasound is transmitted, the switch S3 connects the analog delay circuit 22*b*_and the buffer 22*a* such that a transmission pulse that is transmitted from the transmitter-receiver circuitry 11 is input to the analog delay circuit 22*b*. When reflected waves are received, the switch S3 connects the analog delay circuit 22*b*_and the preamplifier 22*d* such that a reflected-wave signal that is transmitted from the preamplifier 22*d* is input to the analog delay circuit 22*b***.

The switch S2 and the switch S3 are arranged to share the analog delay circuit **22*b*_between transmission and reception. The analog delay circuit 22*b*_may be divided into an analog delay circuit for transmission and an analog delay circuit for reception. In this case, the switch S2 and the switch S3 need not be arranged in the ultrasound probe 1**.

The control circuitry 23 controls the buffers **22*a*, the analog delay circuits 22*b*, the pulsers 22*c*, the preamplifiers 22*d*, the summing circuitry 22*e*, the buffer 22*f*, and the switches S1, S2 and S3. The buffer 22*a*, the analog delay circuit 22*b*, the pulser 22*c*, the preamplifier 22*d*, the summing circuitry 22*e*, the buffer 22*f*, and the switches S1, S2 and S3 are sometimes referred to as control subjects below. For example, the control circuitry 23 controls each control subject such that each control subject performs the above-described operations. For example, the control circuitry 23** controls the respective control subjects by transmitting various control signals respectively to the control subjects.

For example, the control circuitry 23 generates, for the respective channels, various control signals corresponding to the channels and to be supplied to the analog delay circuits **22*b*. An example of a method of generating various control signals performed by the control circuitry 23 will be described. For example, the control circuitry 23 receives transmission delays corresponding to the respective channels from the transmitter-receiver circuitry 11 of the apparatus main unit 10. Based on the transmission delays, the control circuitry 23 generates control signals for causing transmission pulses that are input to the analog delay circuits 22*b*_to be output from the analog delay circuit 22*b* after the transmission delays. The control circuitry 23 transmits the generated control signals to the analog delay circuits 22*b***.

The control circuitry 23 receives reception delays corresponding respectively to channels from the transmitter-receiver circuitry 11 of the apparatus main unit 10. Based on the reception delays, the control circuitry 23 generates control signals for causing reflected-wave signals that are input to the analog delay circuits **22*b*_to be output from the analog delay circuits 22*b*_after the reception delays. The control circuitry 23 transmits the generated control signals to the analog delay circuits 22*b*. The control circuitry 23 is implemented using, for example, the processor. The control circuitry 23** is an example of a controller or a control unit.

Figure 3:
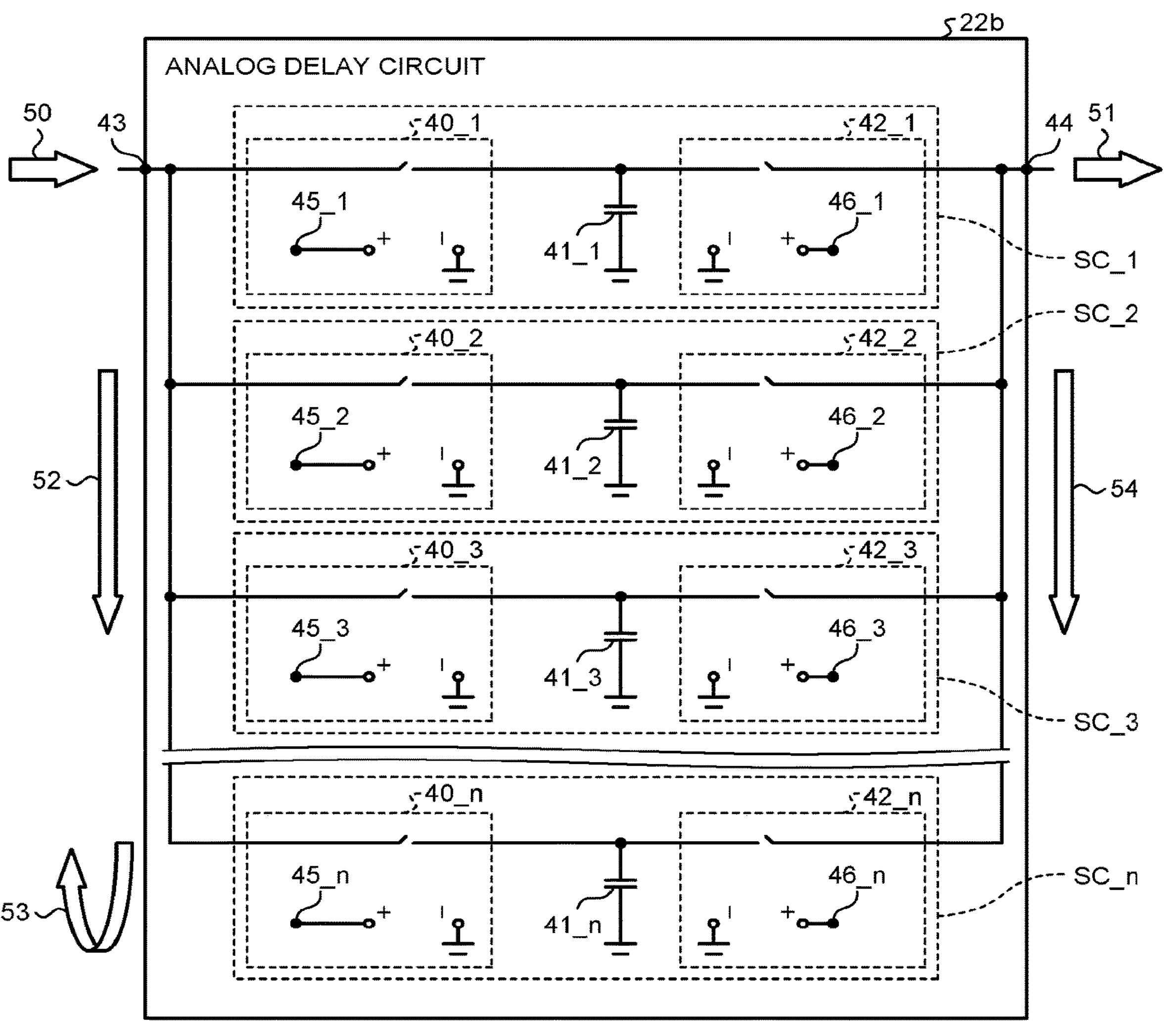
FIG. 3 is a diagram for describing an example of the configuration of an analog delay circuit according to the embodiment.

With reference to FIG. 3, an example of the configuration of the analog delay circuit **22*b*_according to the embodiment will be described. FIG. 3 is a diagram for describing the example of the configuration of the analog delay circuit 22*b***_according to the embodiment.

The analog delay circuit **22*b*_illustrated in FIG. 3 samples parts of a transmission pulse, which is input, in a given sampling period and stores each of the parts of the transmission pulse at multiple sampling time points. The analog delay circuit 22*b*_sequentially reads the respective parts of the transmission pulse that are sampled and stored at sets of timing corresponding to the respective transmission delays and transmits the parts of the transmission pulse as a continuous transmission pulse again to the pulser 22*c***.

The analog delay circuit **22*b*_samples parts of a reflected-wave signal, which is input, in a given sampling period and stores each of the parts of the transmission pulse at multiple sampling time points. The analog delay circuit 22*b*_sequentially reads the respective parts of the reflected-wave signal that are sampled and stored at sets of timing corresponding to the respective reception delays and transmits the parts of the reflected-wave signal as the continuous reflected-wave signal again to the summing circuitry 22*e***.

As illustrated in FIG. 3, the analog delay circuit **22*b* includes a plurality of switched capacitors SC_1 to SC_n (n is a natural number that is 2 or larger), an input terminal 43, and an output terminal 44. The switched capacitor SC_k (k=1, 2, . . . , n) includes a write switch 40**_*k*, a capacitor 41_*k* serving as a memory device, and a read switch 42_*k*.

One end of the write switch 40_*k* is connected to the input terminal 43.

The input terminal 43 is connected to the switch S3. As schematically represented by an arrow 50, a transmission pulse that is transmitted from the transmitter-receiver circuitry 11 and a reflected-wave signal that is transmitted from the preamplifier **22*d* are input to the input terminal 43**.

The other end of the write switch 40_*k* is connected to one end of the capacitor 41_*k*. The other end of the capacitor 41_*k* is grounded.

One end of the read switch 42_*k* is connected to the one end of the capacitor 41_*k*. The other end of the read switch 42_*k* is connected to the output terminal 44.

The output terminal 44 is connected to the switch S2. As schematically represented by an arrow 51, the delayed transmission pulse and the delayed reflected-wave signal are output from the output terminal 44 to the switch S2.

The write switch 40_*k* includes a control signal input terminal 45_*k*.

The control signal input terminal 45_*k* is connected to the control circuitry 23. A control signal for writing (write control signal) is input from the control circuitry 23 to the control signal input terminal 45_*k*. The write control signal will be described below.

The write switches 40_1 to 40_*n* respectively sample parts of transmission pulse that are input according to write control signals. The write switches 40_1 to 40_*n* write the respective sampled parts of the transmission pulse in the capacitors 41_1 to 41_*n*, respectively. Accordingly, the capacitors 41_1 to 41_*n* store the sampled parts of the transmission pulse, respectively.

Similarly, the switches 40_1 to 40_*n* respectively sample parts of reflected-wave signal, which is input, according to write control signals. The write switches 40_1 to 40_*n* write the sampled parts of the reflected-wave signal in the capacitors 41_1 to 41_*n*, respectively. Accordingly, the capacitors 41_1 to 41_*n* respectively store the sampled parts of the reflected-wave signal, respectively.

The read switch 42_*k* includes a control signal input terminal 46_*k*.

The control signal input terminal 46_*k* is connected to the control circuitry 23. A control signal for reading (read control signal) is input from the control circuitry 23 to the control signal input terminal 46_*k*. The read control signal will be described below.

The respective read switches 42_1 to 42_*n* respectively read the parts of the transmission pulse that are written (stored) in the respective capacitors 41_1 to 41_*n* according to the read control signals. The read switches 42_1 to 42_*n* sequentially output the respective read parts of the transmission pulse, thereby outputting the continuous transmission pulse.

Similarly, the respective read switches 42_1 to 42_*n* respectively read the parts of the reflected-wave signal that are written in the respective capacitors 41_1 to 41_*n* according to the read control signals. The read switches 42_1 to 42_*n* sequentially output the respective read parts of the reflected-wave signal, thereby outputting the continuous reflected-wave signal.

Figure 4:
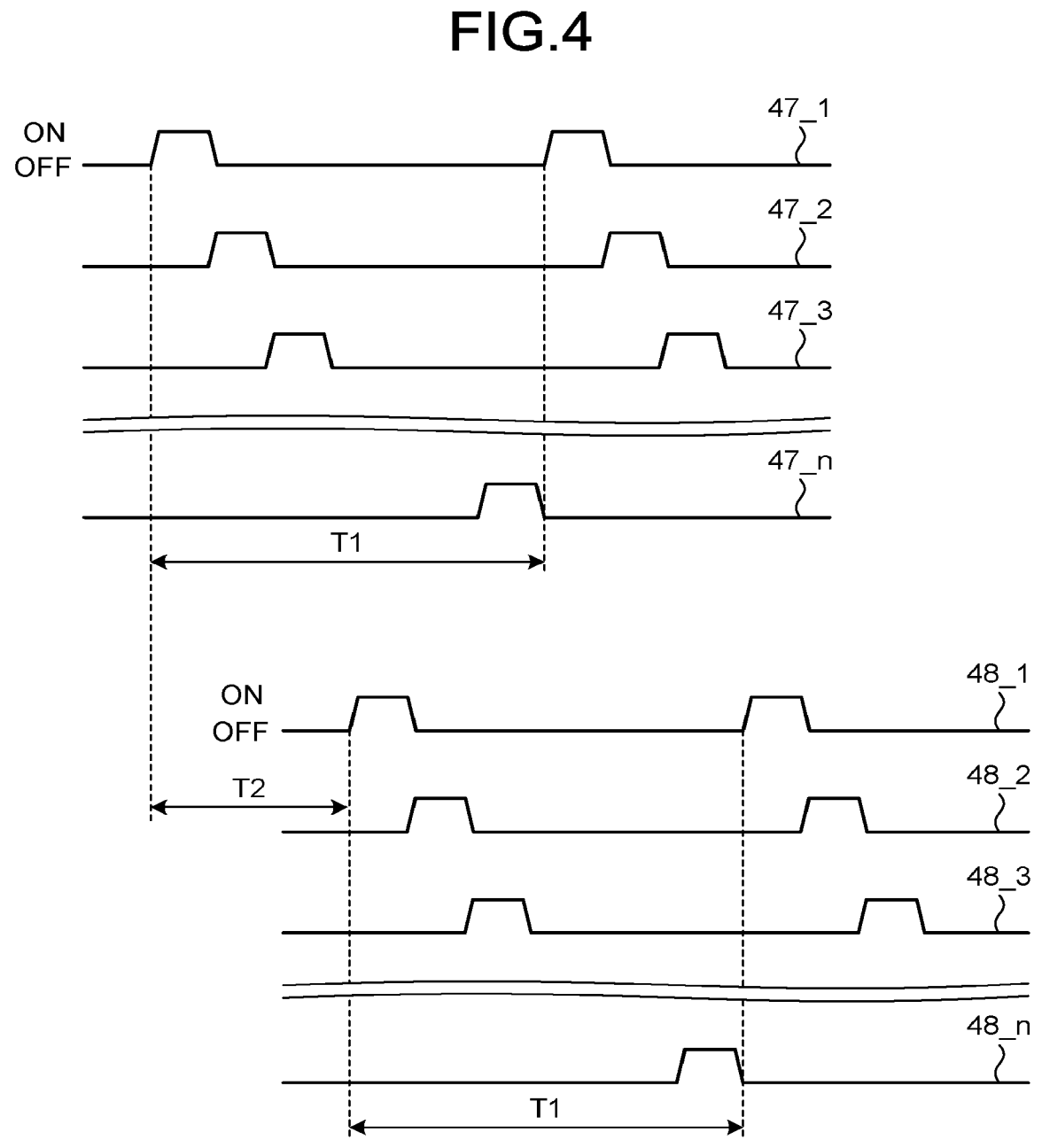

With reference to FIG. 4, an example of the write control signals and the read control signals according to the embodiment will be described. FIG. 4 is a diagram illustrating an example of a plurality of write control signals 47_1 to 47_*n* and a plurality of read control signals 48_1 to 48_*n*.

A write control signal 47_*k* is input to a control signal input terminal 45_*k*. A write switch 40_*k* enables conduction between the input terminal 43 and the capacitor 41_*k* during a period in which the write control signal 47_*k* represents on (high level). In other words, the write switch 40_*k* electrically connects the input terminal 43 and the capacitor 41_*k*. For example, the period in which the write control signal 47_*k* represents on coincides with the period of one clock of a system clock of the ultrasound diagnostic apparatus 100.

The write switch 40_*k* electrically disconnects the input terminal 43 and the capacitor 41_*k* during the period in which the write control signal 47_*k* represents off (low level).

Accordingly, the capacitor 41_*k* accumulates charges during the period in which the write control signal 47_*k* represents on. In other words, the capacitor 41_*k* samples part of a transmission pulse that is input to the input terminal 43 corresponding to the period in which the write control signal 47_*k* represents on and stores the sampled part of the transmission pulse. Similarly, the capacitor 41_*k* samples part of a reflected-wave signal that is input to the input terminal 43 corresponding to the period in which the write control signal 47_*k* represents on and stores the sampled part of the reflected-wave signal.

Part of the transmission pulse and part of the reflected-wave signal corresponding to the period in which the write control signal 47_*k* represents off are not written in the capacitor 41_*k*.

The state in which on is represented sequentially switches over the write control signals 47_1 to 47_*n* approximately successively. Thus, as schematically represented by an arrow 52 (refer to FIG. 3), in the analog delay circuit 22*b*, parts of the transmission pulse are sampled in the given sampling period and are stored in the capacitors 41_1 to 41_*n*, respectively. Similarly, parts of the reflected-wave signal are sampled in the given sampling period and are stored in the capacitors 41_*n* to 41_*n*, respectively.

As illustrated in FIG. 4, the write control signals 47_1 to 47_*n* enter the state in which on is represented in a given period T1. After the write control signal 47_*n* enters the state in which on is represented, the write control signal 47_1 again enters the state in which on is represented. The state in which on is represented sequentially switches over the write control signals 47_1 to 47_*n* approximately successively.

For this reason, in the analog delay circuit 22*b*, as schematically represented by an arrow 53 (refer to FIG. 3), parts of the transmission pulse that are sampled at a plurality of sampling time points after the time point at which the part of the transmission pulse that is stored in the capacitor 41_*n* is sampled are overwritten again in the capacitors 41_1 to 41_*n* sequentially from the capacitor 41_1 to the capacitor 41_*n* and are stored. Similarly, parts of the reflected-wave signal that are sampled at a plurality of sampling time points after the time point at which the part of the reflected-wave signal that is stored in the capacitor 41_*n* is sampled are overwritten again in the capacitors 41_1 to 41_*n* sequentially from the capacitor 41_1 to the capacitor 41_*n* and are stored.

In other words, the analog delay circuit 22*b* periodically writes an ultrasound signal in the capacitors of the analog delay circuit 22*b*.

A read control signal 48_*k* is input to a control signal input terminal 46_*k*. The read switch 42_*k* enables conduction between the output terminal 44 and a capacitor 41_*k* during a period in which a read control signal 48_*k* represents on. In other words, the read switch 42_*k* electrically connects the output terminal 44 and the capacitor 41_*k*. For example, the period in which the read control signal 48_*k* represents on coincides with the period of one clock of the above-described system clock.

The read switch 42_*k* electrically disconnects the output terminal 44 and the capacitor 41_*k* during the period in which a read control signal 48_*k* represents off.

Accordingly, the capacitor 41_*k* emits charges during the period in which the read control signal 48_*k* represents on.

In other words, the read switch 42_*k* reads the part of the transmission pulse that is stored in the capacitor 41_*k* and outputs the read part of the transmission pulse from the output terminal 44. Similarly, the read switch 42_*k* reads the part of the reflected-wave signal that is stored in the capacitor 41_*k* and outputs the read part of the reflected-wave signal from the output terminal 44.

The capacitor 41_*k* keeps storing the part of the stored transmission pulse or the stored part of the reflected-wave signal during the period in which the read control signal 48_*k* represents off.

In the read control signal 48_*k*, the state in which on is represented appears a delay T2 behind the state of the write control signal 47_*k* in which on is represented. The delay T2 is the above-described transmission delay when the transmission pulse is delayed. The delay T2 is the above-described reception delay when a reflected-wave signal is delayed. Accordingly, the part of the transmission pulse, or the part of the reflected-wave signal, that is stored in the capacitor 41_*k* is read after the delay T2 after being stored in the capacitor 41_*k*. The delay T2 is a value unique to each channel and thus is a value unique to each analog delay circuit 22*b*.

The state in which on is represented sequentially switches over the read control signals 48_1 to 48_*n* approximately successively. Thus, as schematically represented by an arrow 54 (refer to FIG. 3), in the analog delay circuit 22*b*, the sampled parts of the transmission pulse are read from the capacitors 41_*n* to 41_*n*, respectively. Similarly, the sampled parts of the reflected-wave signal are read from the capacitors 41_*n* to 41_*n*, respectively.

Like the write control signals 47_1 to 47_*n*, the read control signals 48_1 to 48_*n* enter the state in which on is represented in the given period T1. After the read control signal 48_*n* enters the state in which on is represented, the read control signals 48_1 again enters the state in which on is represented. The state in which on is represented sequentially switches over the read control signals 48_1 to 48_*n* approximately successively.

For this reason, in the analog delay circuit 22*b*, after the part of the transmission pulse is read from the capacitor 41_*n*, the parts of the transmission pulse that are sampled at the sampling time points after the sampling time point at which the part of the transmission pulse that is stored in the capacitor 41_*n* is sampled are read from the capacitor 41_1 to 41_*n* sequentially from the capacitors 41_1 to 41_*n* again. Similarly, after the part of the reflected-wave signal is read from the capacitor 41_*n*, the parts of the reflected-wave signal that are sampled at the sampling time points after the sampling time point at which the part of the reflected-wave signal that is read from the capacitor 41_*n* is sampled are read from the capacitors 41_1 to 41_*n* sequentially from the capacitor 41_1 to 41_*n* again. In the analog delay circuit 22*b*, such read operations are repeated.

In other words, the analog delay circuit 22*b* periodically reads an ultrasound signal from the capacitors of the analog delay circuit 22*b*.

The above-described period T1 is a value corresponding to the number of the capacitors 41_1 to 41_*n*. Note that the number of the capacitors 41_1 to 41_*n* is a value corresponding to the maximum delay in the delay processing that is performed by the analog delay circuit 22*b*.

As described above, a write control signal 47_*k* and a read control signal 48_*k* have periodicity in which the state in which on is represented recurs every period T1. Because of such periodicity of the write control signal 47_*k* and the read control signal 48_*k*, a frequency component (spurious emission) that is not intended in design is superimposed onto the reflected-wave signal as a noise component. Such noise is also referred to as periodic noise. The period of the periodic noise (noise period) is the period T1. The periodic noise is superimposed onto the reflected-wave signals and thus the periodic noise is also superimposed onto the summing signal.

For example, noise components are superimposed onto the reflected-wave signals that are output from the analog delay circuits 22*b*_and the summing signal that is output from the summing circuitry 22*e*. Such noise components result in a virtual image on an ultrasound image.

Figure 5:
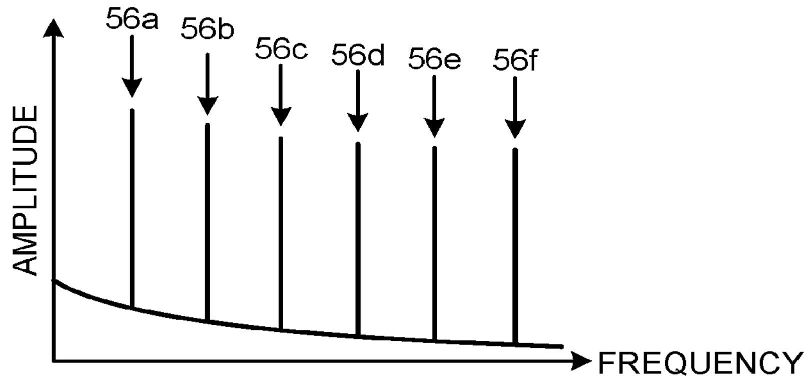
FIG. 5 is a diagram for describing an example of noise components that are superimposed onto a reflected-wave signal.

FIG. 5 is a diagram for describing an example of the noise components that are superimposed onto a reflected-wave signal. FIG. 5 represents the result of frequency analysis on the reflected-wave signal. The horizontal axis represents the frequency and the vertical axis represents the amplitude.

As illustrated in FIG. 5, the component of a fundamental frequency (1/T1) represented by an arrow 56*a* contains a noise component. The components of multiples of the fundamental frequency ((2/T1), (3/T1), (3/T1), (4/T1), (5/T1) and (6/T1)) contain noise components. The component of the fundamental frequency (1/T1) is also referred to as a fundamental wave component. The component of twice the fundamental frequency (2/T1), the component of three times the fundamental frequency (3/T1), the component of four times the fundamental frequency (4/T1), the component of five times the fundamental frequency (5/T1), and the component of six times the fundamental frequency (6/T1) are also respectively referred to as a second harmonic component, a third harmonic component, a fourth harmonic component, a fifth harmonic component, and a sixth harmonic component. Although not illustrated in FIG. 5, the component of seven times the fundamental frequency (7/T1) contains a noise component. The component of seven times the fundamental frequency is also referred to as a seventh harmonic component.

From among the components, the fundamental wave component, the third harmonic component, the fifth harmonic component, and the seventh harmonic component are also referred to as odd harmonic components. The second harmonic component, the fourth harmonic component, and the sixth harmonic component are also referred to as even harmonic components.

Figure 6:
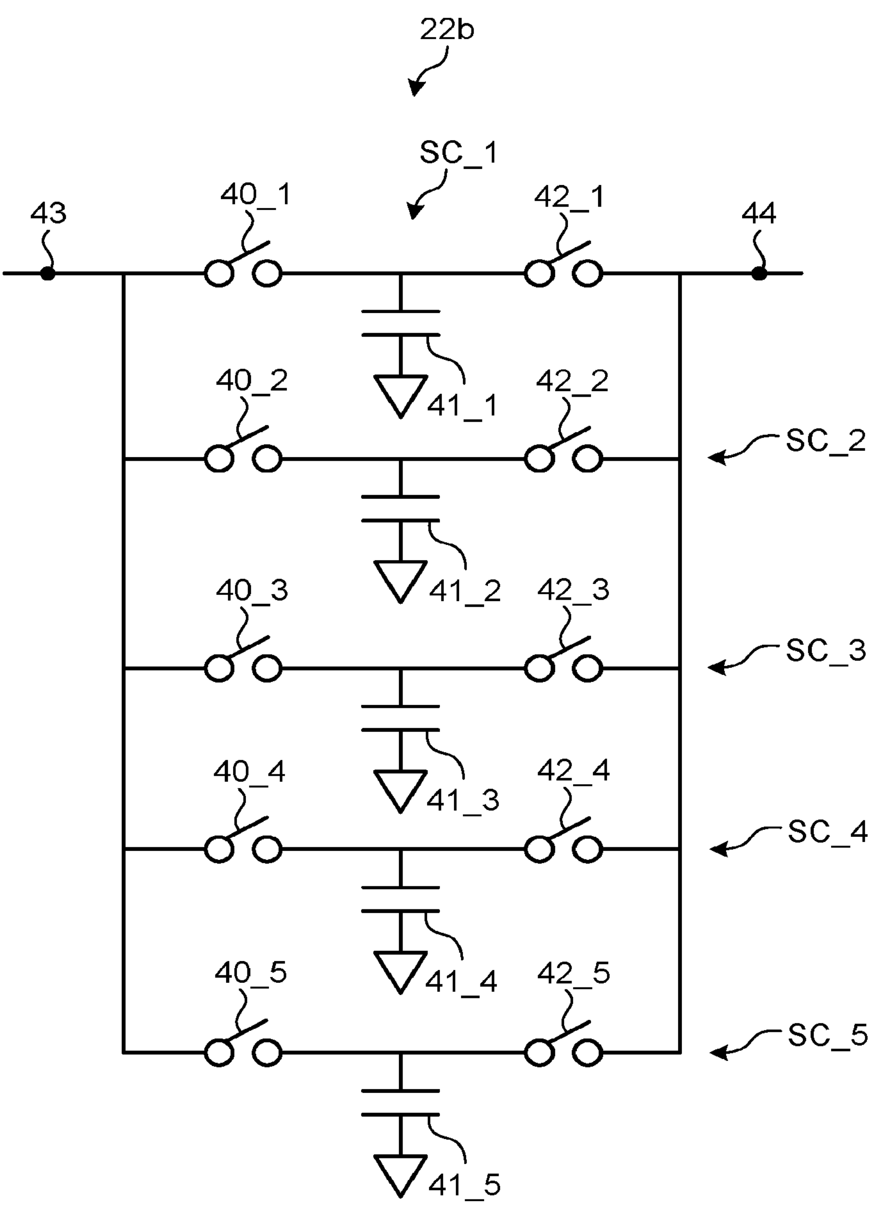
FIG. 6 is a diagram schematically illustrating an analog delay circuit in the case where the number of switched capacitors that the analog delay circuit illustrated in FIG. 3 includes is “5”
Figure 7:
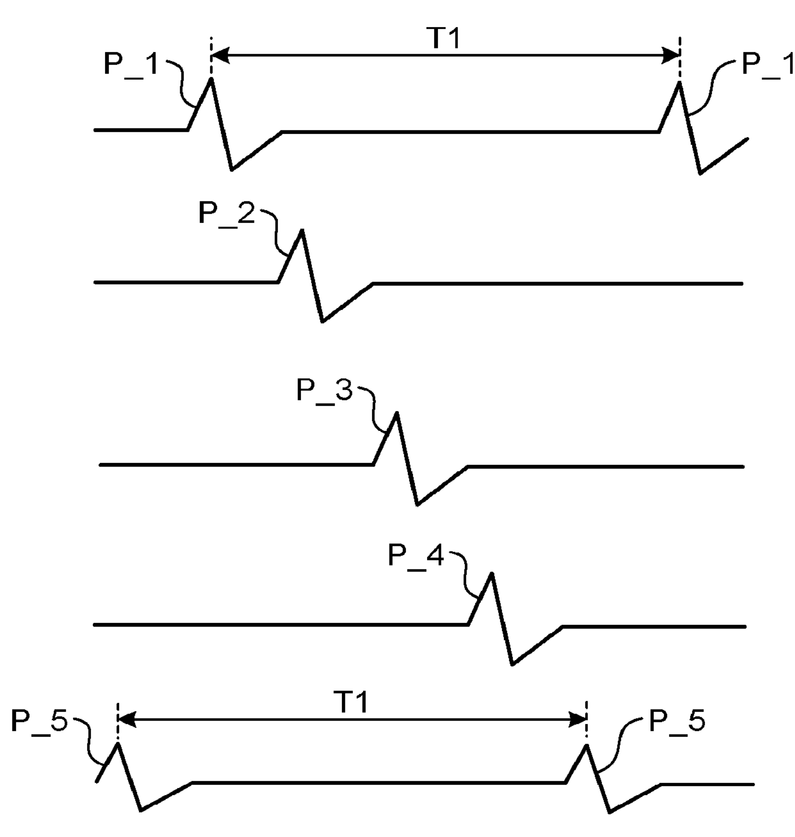
FIG. 7 is a diagram illustrating an example of a pattern of periodic noise that is superimposed onto output signals that are output respectively from the switched capacitors.
Figure 7:
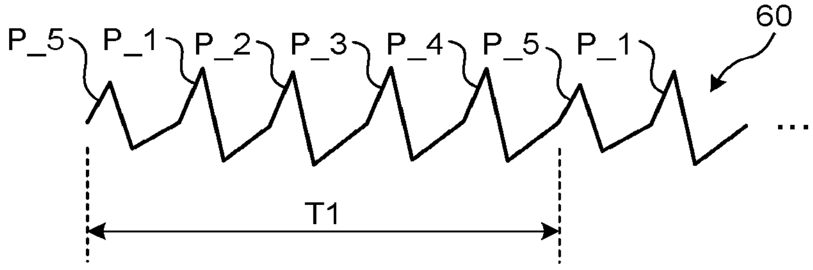

With reference to FIGS. 6 and 7, an example of the reason why periodic noise that is superimposed onto the reflected-wave signal will be described. FIG. 6 is a diagram schematically illustrating the analog delay circuit 22*b*_in the case where the number of the switch capacitors SC_1 to SC_n is 5. FIG. 7 is diagram illustrating an example of a pattern of the periodic noise that is superimposed onto the output signals that are output respectively from the switched capacitors SC_1 to SC_5.

As illustrated in FIG. 6, the length of an interconnect connecting the input terminal 43 and a switched capacitor SC_m (m=1, 2, . . . , 5) is a length corresponding to the position of the switched capacitor SC_m. For example, when the length of the interconnect connecting the input terminal 43 and the switched capacitor SC_m is denoted by "L1_*m*", in the case where the circuit layout of the analog delay circuit 22*b* is as illustrated in FIG. 6, "L1_1", "L1_2", "L1_3", "L1_4" and "L1_5" are in an ascending order from "L1_1" to "L1_6" and are different from one another.

As illustrated in FIG. 6, the length of an interconnect connecting the output terminal 44 and the switched capacitor SC_m is a length corresponding to the position of the switched capacitor SC_m. For example, when the length of the interconnect connecting the output terminal 44 and the switched capacitor SC_m is denoted by "L2_*m*", in the case where the circuit layout of the analog delay circuit 22*b* is as illustrated in FIG. 6, "L2_1", "L2_2", "L2_3", "L2_4" and "L2_5" are in an ascending order from "L2_1" to "L2_5" and are different from one another.

Thus, the parasitic impedance differs in each switched capacitor SC_m.

The length of an interconnect connecting the control circuitry 23 and the switched capacitor SC_m is a length corresponding to the position of the switched capacitor SC_m. For example, when the length of the interconnect connecting the control circuitry 23 and the switched capacitor SC_m is denoted by "L3_*m*", "L3_1", "L3_2", "L3_3", "L3_4" and "L3_5" are different from one another. Thus, the rate of rise and the rate of decrease in the waveform of the control signal that is input differ in each switched capacitor SC_m. Accordingly, the degree of feedthrough differs in each switched capacitor SC_m. In other words, part of the control signal is superimposed as noise on the output signal that is output from the switched capacitor SC_m and the degree of noise differs in each switched capacitor SC_m.

Accordingly, when the pattern of periodic noise that is superimposed onto the output signal that is output from the switched capacitor SC_m is denoted by "P_m", as illustrated in FIG. 7, a pattern P_1, a pattern P_2, a pattern P_3, a pattern P_4, and a pattern P_5 are different from one another. The set of the patterns P_1 to P_5 appears repeatedly. When the noise that is superimposed in each switched capacitor SC_m has the same waveform, the noise period is equal to the sampling period. In this case, the frequency of noise is not problematic because the noise frequency is out of the frequency band of the ultrasound probe 1; however, when the waveform of the noise that is superimposed in each switched capacitor SC_m differs, as illustrated in FIG. 7, the periodic noise that is noise with the periodicity of the period T1 is superimposed onto the reflected-wave signal 60 that is output from the analog delay circuit 22*b*. The noise frequency is within the ultrasound frequency band and thus is problematic.

Figure 8:
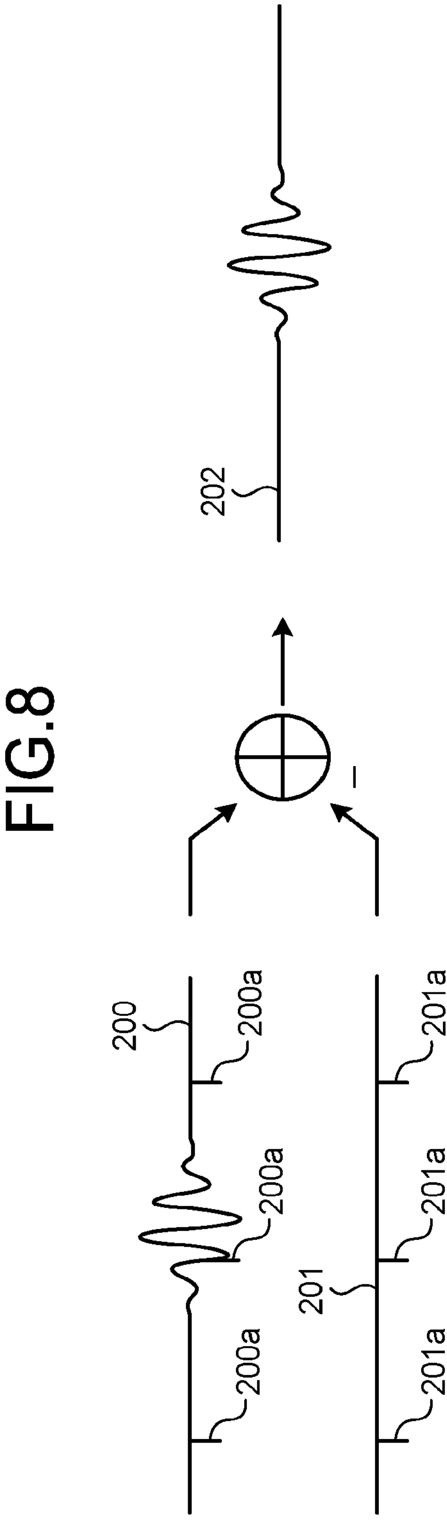
FIG. 8 is a diagram for describing an example of processing for reducing the periodic noise.

In order to reduce the periodic noise, performing the process to be described below is considered. FIG. 8 is a diagram for describing an example of processing to reduce the periodic noise.

FIG. 8 illustrates a reflected-wave signal 200, a cancellation signal 201 and an image signal 202. Periodic noise 200*a* is superimposed onto the reflected-wave signal 200.

The cancellation signal 201 is a reflected-wave signal that a transducer of the ultrasound probe outputs without transmitting ultrasound. In other words, the cancellation signal 201 is a reflected-wave signal not containing any reflected-wave of ultrasound from the subject. Periodic noise 201*a* is superimposed onto the cancellation signal 201.

The receiver of the transmitter-receiver circuitry subtracts the cancellation signal 201 from the reflected-wave signal 200, thereby calculating the image signal 202 that is used for imaging.

As illustrated in FIG. 8, the periodic noise 200*a* that is superimposed onto the reflected-wave signal 200 is reduced in the image signal 202. As described above, the periodic noise is reduced in the image signal 202.

When one image signal 202 is generated, however, it is necessary to perform subtraction processing of subtracting the cancellation signal 201 from the reflected-wave signal 200. In other words, when ultrasound image data corresponding to one rate is generated, it is necessary to perform a transmitting-receiving operation twice. Thus, there is a risk that the frame rate lower.

When one image signal 202 is generated, subtraction processing using two signals (the reflected-wave signal 200 and the cancellation signal 201) is performed. For example, when the number of signals to be added or subtracted is "s", the volume of random noise other than the periodic noise resulting from periodicity is proportional to "$s^{1/2}$". In the case where the periodic noise is reduced according to the above-described method, when using one reflected-wave signal 200 as the image signal 202 to be used for imaging is taken as a reference, the volume of random noise is multiplied by "$2^{1/2}$" and increases.

The ultrasound probe 1 according to the embodiment executes processing to be described below to reduce the noise that is contained in the summing signal while inhibiting the frame rate from lowering.

Figure 9:
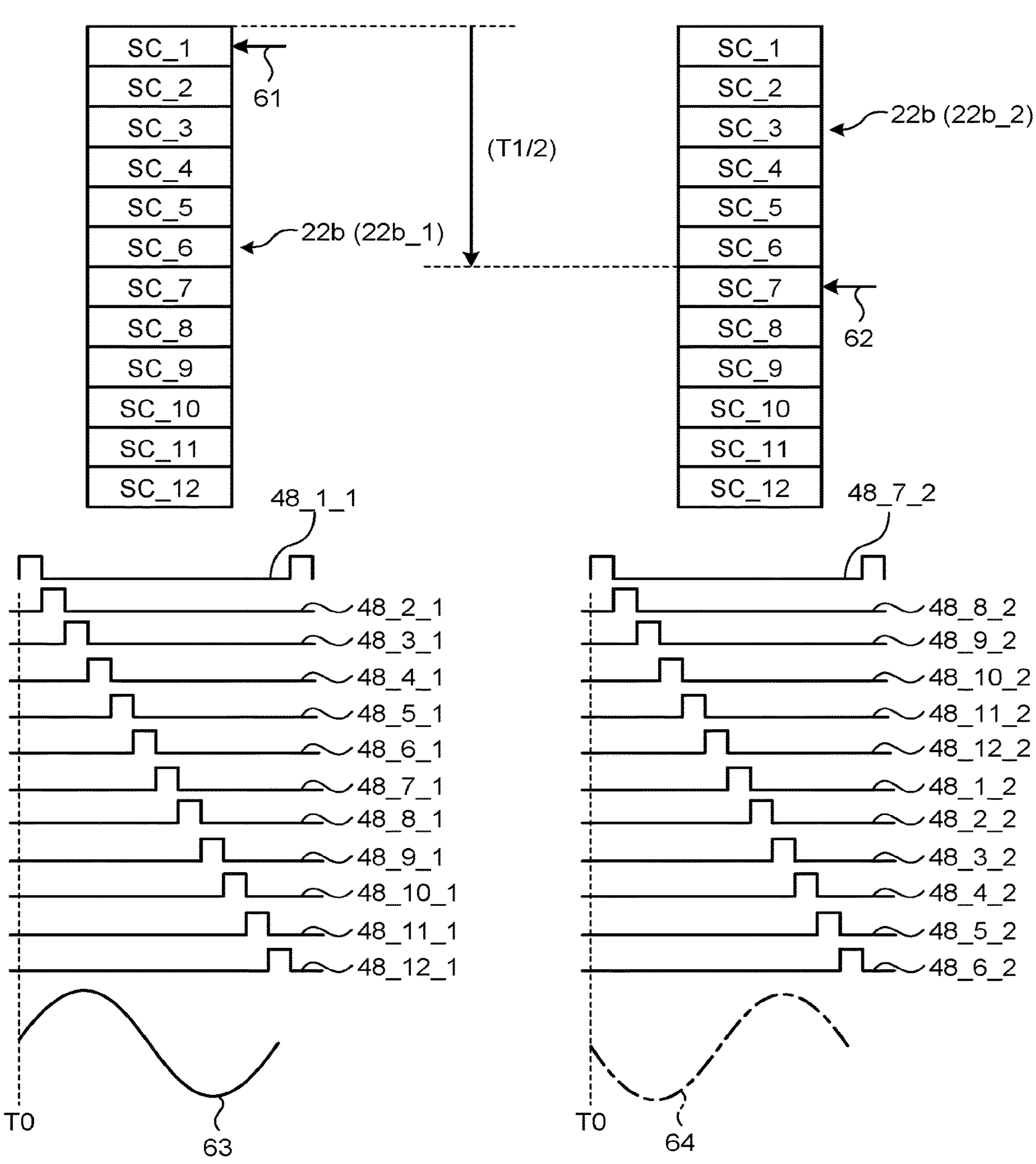
FIG. 9 is a diagram for describing an example of processing that is executed by a control circuit according to the embodiment.

FIG. 9 is a diagram for describing an example of processing that the control circuitry 23 executes according to the embodiment. For example, the control circuitry 23 determines two channels in a pair from the channels of the same subarray. In the following description, two channels in a pair are sometimes referred to as a pair channel. For example, the control circuitry 23 determines a set of any two channels of the channels in the same subarray as a pair channel. For example, the control circuitry 23 may determine one pair channel from multiple channels in the same subarray or may determine as many as pair channels. In other words, the control circuitry 23 determines at least one pair channel in each subarray. The control circuitry 23 performs processing to be described below on each pair channel.

As illustrated in FIG. 9, the control circuitry 23 controls read positions such that the read position in the analog delay circuit 22*b*_corresponding to one of the channels of a pair channel and the read position of the analog delay circuit 22*b*_corresponding to the other channel at an identical time are shifted from each other by a half period (T1/2) of a noise period T1. In the following description, the analog delay circuit 22*b*_corresponding to the one channel is denoted by "analog delay circuit 22*b*_1" and the analog delay circuit 22*b*_corresponding to the other channel is denoted by "analog delay circuit 22*b*_2".

For example, each of the analog delay circuits 22*b*_1 and 22*b*_2 illustrated in FIG. 9 includes 12 switched capacitors SC_1 to SC_12. In the following description, the twelve switched capacitors SC_1 to SC_12 are sometimes simply referred to as "switched capacitors SC" when the switched capacitors SC_1 to SC_12 are not distinguished from one another. The above-described "read position" refers to a switched capacitor SC in which the reflected-wave signal is read. The number of the switched capacitors SC is not limited to 12 and it may be any number. All the switched capacitors SC contained in the analog delay circuit 22*b* need not necessarily be used and, for example, only part of the switched capacitors SC_1 to SC_12, such as the switched capacitors SC_1 to SC_6, may be used.

In the case illustrated in FIG. 9, the 12 switched capacitors SC correspond to the noise period T1 and the six switched capacitors SC correspond to the half period (T1/2) of the noise period T1. In other words, the switched capacitors SC that are half as many as all the switched capacitors that are used in one analog delay circuit 22*b* correspond to the half period (T1/2) of the noise period T1.

The control circuitry 23 makes the read position in which the reflected-wave signal is read from one of the capacitors

41_1 to 41_12 of the analog delay circuit 22*b*__1 and the read position in which the reflected-wave signal is read from one of the capacitors 41_1 to 41_12 of the analog delay circuit 22*b*__2 at identical times different from each other. The read position in which the reflected-wave signal is read from one of the capacitors 41_1 to 41_12 of the analog delay circuit 22*b*__1 is an example of the first read position. The read position in which the reflected-wave signal is read from one of the capacitors 41_1 to 41_12 of the analog delay circuit 22*b*_2 is an example of the second read position.

For example, the control circuitry 23 controls the read positions such that, as schematically represented by an arrow 61, the read position in the analog delay circuit 22*b*_1 is the switched capacitor SC_1 of the analog delay circuit 22*b*_1 at a time T0.

As schematically represented by an arrow 62, the control circuitry 23 controls the read positions such that the read position in the analog delay circuit 22*b*_2 is the switched capacitor SC_7 of the analog delay circuit 22*b*_2 at the time T0. The switched capacitor SC_7 of the analog delay circuit 22*b*_2 corresponds to the switched capacitor SC that is shifted by six switched capacitors SC from the switched capacitor SC_1.

A read control signal 48_*k* that is input to a switched capacitor SC_k of the analog delay circuit 22*b*_1 is denoted by "48_*k*_1". A read control signal 48_*k* that is input to a switched capacitor SC_k of the analog delay circuit 22*b*_2 is denoted by "48_*k*_2".

As illustrated in FIG. 9, at the time T0, in the analog delay circuit 22*b*_1, a read control signal 48_1_1 turns from the state in which off is represented into the state in which on is represented. The state in which on is represented sequentially switches over a plurality of read control signals 48_1_1 to 48_12_1 approximately successively. In other words, the parts of the reflected-wave signal that are sequentially read by the switched capacitors SC_1 to SC_12 of the analog delay circuit 22*b*_1 are output and accordingly the continuous reflected-wave signal is output from the analog delay circuit 22*b*_1.

In other words, the analog delay circuit 22*b*_1 delays the reflected-wave signal in the channel corresponding to the analog delay circuit 22*b*_1 using the capacitors 41_1 to 41_*n*. The analog delay circuit 22*b*_1 is an example of the first delay circuit. The channel corresponding to the analog delay circuit 22*b*_1 is an example of the first channel. The reflected-wave signal is an example of the ultrasound signal.

On the other hand, at the time T0, in the analog delay circuit 22*b*_2, a read control signal 48_7_2 turns from the state in which off is represented into the state in which on is represented. The state in which on is represented switches sequentially over a plurality of read control signals 48_7_2 to 48_12_2 and 48_1_2 to 48_6_2 approximately successively. In other words, the parts of the reflected-wave signal that are sequentially read by the switched capacitors SC_7 to SC_12 and SC_1 to SC_6 of the analog delay circuit 22*b*_2 are output and accordingly the continuous reflected-wave signal is output from the analog delay circuit 22*b*_2.

In other words, the analog delay circuit 22*b*_2 delays the reflected-wave signal in the channel corresponding to the analog delay circuit 22*b*_2 using the capacitors 41_1 to 41_*n*. The analog delay circuit 22*b*_2 is an example of the second delay circuit. The channel corresponding to the analog delay circuit 22*b*_2 is an example of the second channel.

For example, the number of the capacitors 41_*n* to 41_*n* that are used by the analog delay circuit 22*b*_1 and the number of the capacitors 41_1 to 41_*n* that are used by the analog delay circuit 22*b*_2 are equal to each other.

FIG. 9 illustrates a waveform 63 representing a phase of the periodic noise of the period T1 that is superimposed on the reflected-wave signal that is output from the analog delay circuit 22*b*_1. FIG. 9 further illustrates a waveform 64 representing a phase of the periodic noise of the period T1 that is superimposed on the reflected-wave signal that is output from the analog delay circuit 22*b*_2. In other words, the waveform 63 is also a waveform representing the phase of the reflected-wave signal that is output from the analog delay circuit 22*b*_1. Similarly, the waveform 64 is also a waveform representing the phase of the reflected-wave signal that is output from the analog delay circuit 22*b*_2. The waveform 63 and the waveform 64 are, for example, sine waves.

As illustrated in FIG. 9, the shift between the phase of the waveform 63 and the phase of the waveform 64 (phase difference) is 180 degrees at an identical time. The reason why the phase difference is 180 degrees is that the read position in the analog delay circuit 22*b*_1 at a given time T and the read position in the analog delay circuit 22*b*_2 at the time T are shifted from each other by the half period (T1/2) of the noise period T1. The phase difference is 180 degrees as described above and accordingly the reflected-wave signal that is output from the analog delay circuit 22*b*_1 and the reflected-wave signal that is output from the analog delay circuit 22*b*_2 are summed by the summing circuitry 22*e*, so that an adding signal in which the periodic noise is cancelled is obtained.

Thus, according to the ultrasound probe 1 according to the embodiment, it is possible to obtain a summing signal in which periodic noise is reduced.

When generating ultrasound image data, the ultrasound probe 1 according to the embodiment uses the reflected-wave signals without using the above-described cancellation signal 201. For this reason, according to the ultrasound probe 1 according to the embodiment, when the case illustrated in FIG. 8 is taken as a reference, ultrasound image data is obtained without extra subtraction and thus random noise is not increased.

In the ultrasound probe 1 according to the embodiment, the summing circuitry 22*e* simultaneously performs beamforming and noise cancellation. Accordingly, in the ultrasound probe 1 according to the embodiment, when ultrasound image data is generated, the subtraction processing using the cancellation signal 201 described above with reference to FIG. 8 need not be performed. For this reason, according to the ultrasound probe 1 according to the embodiment, compared to the case illustrated in FIG. 8, the transmitting-receiving operation is performed only once to obtain ultrasound image data of one rate and it is thus possible to inhibit the frame rate from lowering.

Thus, according to the ultrasound probe 1 according to the embodiment, it is possible to reduce noise contained in an adding signal while inhibiting the frame rate from lowering.

In order to shift the read positions in the analog delay circuit 22*b*_1 and the read positions in the analog delay circuit 22*b*_2 from each other by the half period (T1/2) of the noise period T1, the control circuitry 23 has to appropriately control the write start positions in the analog delay circuit 22*b*_1 and the write start positions in the analog delay circuit 22*b*_2 before controlling the read positions. Note that a write start position refers to a switched capacitor SC in which writing a reflected-wave signal is started at a write start time (for example, the time T3 to be described below in FIG. 11).

For example, the control circuitry 23 controls the write start positions in consideration of a difference between the reception delay corresponding to the analog delay circuit 22_b__1 and the reception delay corresponding to the analog delay circuit 22_b__2 (delay difference). An example of the control on the write start positions performed by the control circuitry 23 will be described.

Assume that the reception delay is represented by the number of system clocks. For example, when the reception delay is "r", the actual reception delay corresponds to the time of "r" clocks of the system clock. For example, when the reception delay is "r", reading part of the reflected-wave signal from a capacitor 41__k_ is started at timing when the time of "r+1" clocks of the system clock elapses from the timing when writing the part of the reflected-wave signal in the capacitor 41__k_ is started. In other words, when the reception delay is "r", reading part of the reflected-wave signal from the capacitor 41__k_ is started at the timing when the time of "r" clocks of the system clock elapses from the timing when writing the part of the reflected-wave signal in the capacitor 41__k_ ends. In the description herein, the period in which a write control signal 47__k_ represents on coincides with the period of one clock of the system clock.

In the description of the embodiment, the case in which the reception delay corresponding to the analog delay circuit 22_b__1 is "0" and the reception delay corresponding to the analog delay circuit 22_b__2 is "3" will be exemplified and described. Note that the reception delay corresponding to the analog delay circuit 22_b__1 and the reception delay corresponding to the analog delay circuit 22_b__2 are not limited to them.

Figure 10:
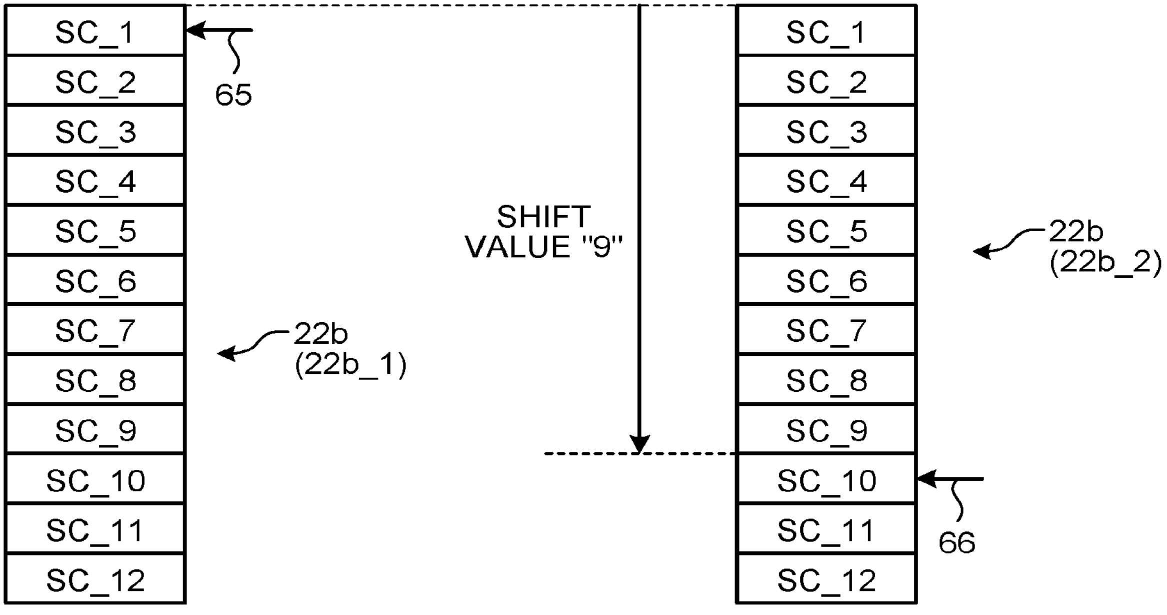
FIG. 10 is a diagram for describing an example of processing that is executed by the control circuit according to the embodiment.

With reference to FIG. 10, the case where the control circuitry 23 controls the write start positions after determining a pair channel will be described. FIG. 10 is a diagram for describing an example of processing that the control circuitry 23 executes according to the embodiment.

Figure 11:
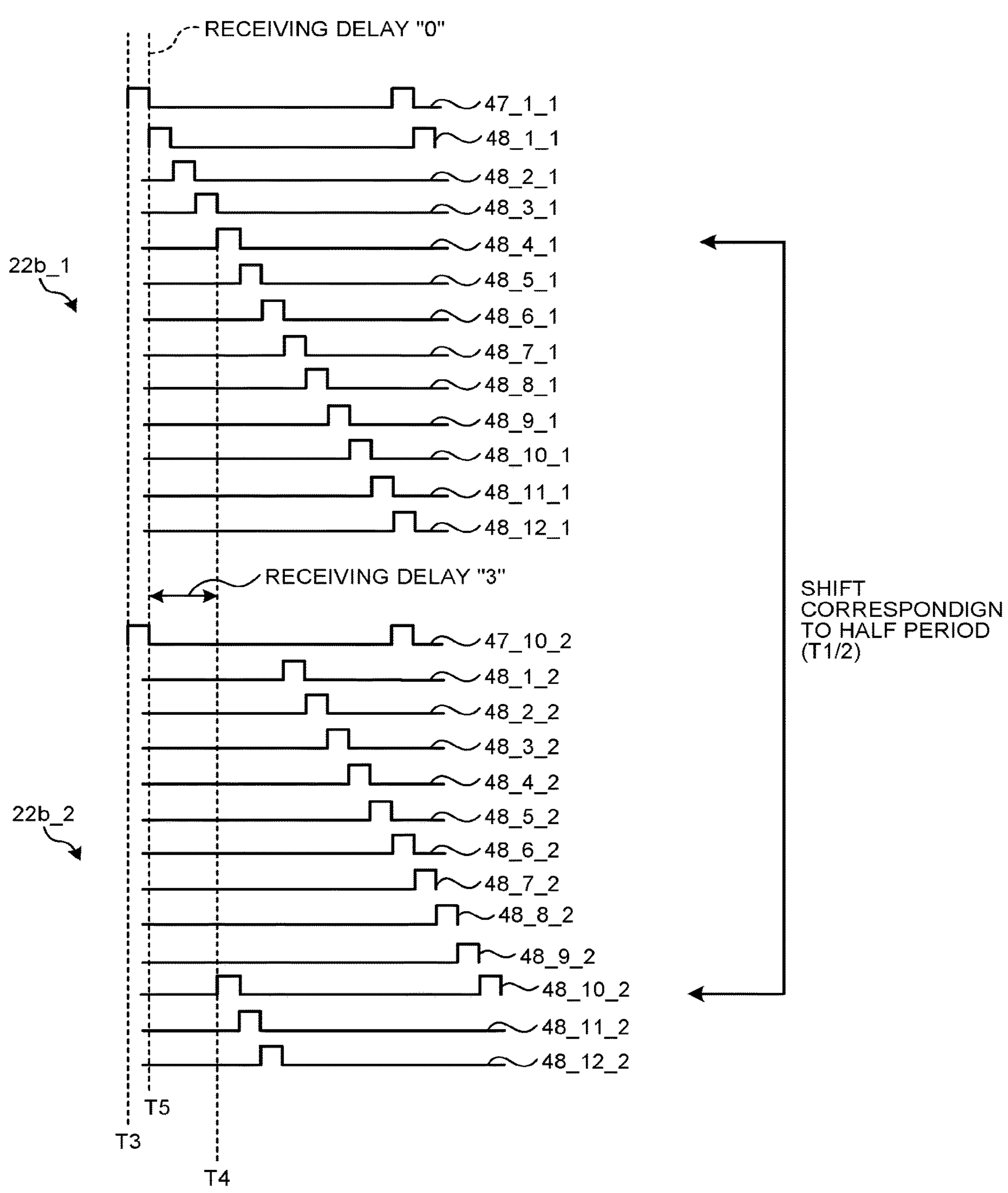
FIG. 11 is a diagram illustrating an example of write control signals and read control signals that are input to the two analog delay circuits that are illustrated in FIG. 10.

As illustrated in FIG. 10, the control circuitry 23 controls the write start positions such that, as schematically represented by an arrow 65, the write start position in the analog delay circuit 22_b__1 is the switched capacitor SC_1 of the analog delay circuit 22_b__1 at a write start time T3 (refer to FIG. 11). The control circuitry 23 may determine, as a write start position, any one switched capacitor SC of the switched capacitors SC_1 to SC_12 of the analog delay circuit 22_b__1.

As schematically represented by an arrow 66, the control circuitry 23 controls the write start positions such that the write start position in the analog delay circuit 22_b__2 is the switched capacitor SC_10 of the analog delay circuit 22_b__2 at the write start time T3. Specifically, the control circuitry 23 calculates a delay difference "3" by subtracting the reception delay "0" corresponding to the analog delay circuit 22_b__1 from the reception delay "3" corresponding to the analog delay circuit 22_b__2. The control circuitry 23 adds the delay difference "3" to the number "6" of the switched capacitors SC corresponding to the half period (T1/2) of the noise period T1, thereby calculating a value "9" of the shift (shift value) from the write start position (the switched capacitor SC_1) in the analog delay circuit 22_b__1.

The control circuitry 23 then determines, as the write start position in the analog delay circuit 22_b__2, the switched capacitor SC_10 of the analog delay circuit 22_b__2 that is shifted by the shift value of "9" from the write start position (the switched capacitor SC_1) in the analog delay circuit 22_b__1. The control circuitry 23 controls the write start positions such that the write start position in the analog delay circuit 22_b__2 is the switched capacitor SC_10 of the analog delay circuit 22_b__2. In other words, the control circuitry 23 makes the write start position in which writing the reflected-wave signal in one of the capacitors 41_1 to 41__n_ of the analog delay circuit 22_b__1 is started and the write start position in which writing the reflected-wave signal in one of the capacitors 41_1 to 41__n_ of the analog delay circuit 22_b__2 is started different from each other.

The write start position in which writing the reflected-wave signal in one of the capacitors 41_1 to 41__n_ of the analog delay circuit 22_b__1 is started is an example of a first write start position. The write start position in which writing the reflected-wave signal in one of the capacitors 41_1 to 41__n_ of the analog delay circuit 22_b__2 is started is an example of a second write start position.

The control circuitry 23 calculates a shift value based on a number that is half of the number of the capacitors (capacitors used) contained in the analog delay circuit 22_b__1 or the analog delay circuit 22_b__2. Based on the shift value, the control circuitry 23 makes the read position in which the reflected-wave signal is read from one of the capacitors 41_1 to 41_12 of the analog delay circuit 22_b__1 and the read position in which the reflected-wave signal is read from one of the capacitors 41_1 to 41_12 of the analog delay circuit 22_b__2 at identical times different from each other. In other words, based on the number of the capacitors 41_1 to 41__n_ contained in the analog delay circuit 22_b__1 or the analog delay circuit 22_b__2, the control circuitry 23 makes the read position in which the reflected-wave signal is read from one of the capacitors 41_1 to 41_12 of the analog delay circuit 22_b__1 and the read position in which the reflected-wave signal is read from one of the capacitors 41_1 to 41_12 of the analog delay circuit 22_b__2 at identical times different from each other.

FIG. 11 is a diagram illustrating an example of the write control signals and the read control signals that are input to the two analog delay circuits 22_b__1 and 22_b__2. A read control signal 48__k_ that is input to a switched capacitor SC_k of the analog delay circuit 22_b__1 is represented by "48__k__1". A read control signal 48__k_ that is input to a switched capacitor SC_k of the analog delay circuits 22_b__2 is denoted by "48__k__2". Furthermore, a write control signal 47__k_ that is input to the switched capacitor SC_k of the analog delay circuits 22_b__1 is denoted by "47__k__1". A write control signal 47__k_ that is input to the switched capacitor SC_k of the analog delay circuits 22_b__2 is denoted by "47__k__2".

As illustrated in FIG. 11, in the analog delay circuits 22_b__1, at the write start time T3, a write control signal 47_1_1 turns from the state in which off is represented into the state in which on is represented. At and after the timing (a time T5) when the time corresponding to the reception delay "0" has elapsed from the write start time T3, the state in which on is represented sequentially switches over the read control signals 48_1_1 to 48_12_1 approximately successively.

On the other hand, in the analog delay circuit 22_b__2, at the write start time T3, the write control signal 47_10_2 turns from the state in which off is represented into the state in which on is represented. At and after the timing (a time T4) when the time corresponding to the reception delay "3" has elapsed from the write start time T3, the state in which on is represented sequentially switches over the read control signals 48_10_2 to 48_12_2 and 48_1_2 to 48_9_2 approximately successively.

As the read control signal 48_10_2 indicates, at the time T4, reading part of the reflected-wave signal is started in the switched capacitor SC_10 of the analog delay circuit 22_b__2. As the read control signal 48_4_1 indicates, at the time T4, reading part of the reflected-wave signal is started in the switched capacitor SC_4 of the analog delay circuit **22*b*_1**.

In other words, at the time T4, the read position in the analog delay circuit **22*b*_1 and the read position in the analog delay circuit 22*b*_2 are shifted from each other by the half period (T1/2) of the noise period T1. At other times after the time T4, similarly, the read position in the analog delay circuit 22*b*_1 and the read position in the analog delay circuit 22*b*_2** are shifted from each other by the half period (T1/2) of the noise period T1.

The control circuitry 23 controls the write start positions according to the above-described method, thereby shifting the read position in the analog delay circuit **22*b*_1 and the read position in the analog delay circuit 22*b*_2 from each other by the half period (T1/2) of the noise period T1. Specifically, the control circuitry 23 makes the write start position in the analog delay circuit 22*b*_1 and the write start position in the analog delay circuit 22*b*_2 different from each other such that the phase difference between the reflected-wave signal that is delayed by the analog delay circuit 22*b*_1 and the reflected-wave signal that is delayed by the analog delay circuit 22*b*_2 at identical times is 180 degrees, thereby shifting the two read positions by the half period (T1/2) of the noise period T1. In this manner, the control circuitry 23 makes the read position in the analog delay circuit 22*b*_1 and the read position in the analog delay circuit 22*b*_2 different from each other such that the phase difference between the reflected-wave signal that is delayed by the analog delay circuit 22*b*_1 and the reflected-wave signal that is delayed by the analog delay circuit 22*b*_2** at the identical time is 180 degrees.

As a result, according to the ultrasound probe 1 according to the embodiment, it is possible to reduce the above-described odd harmonic components (such as the fundamental wave component, the third harmonic component, the fifth harmonic component, and the seventh harmonic component).

Figure 12:
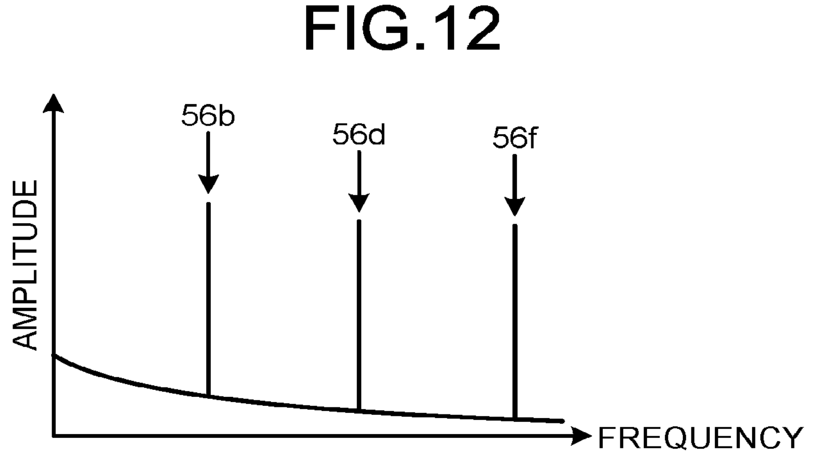
FIG. 12 is a diagram for describing an example of noise components that are superimposed onto a summing signal that is output from a summing circuit according to the embodiment.

FIG. 12 is a diagram for describing an example of noise components that are superimposed onto a summing signal that is output from the summing circuitry **22*e* according to the embodiment. FIG. 12 illustrates the result of frequency analysis on the summing signal. The horizontal axis represents the frequency and the vertical axis represents the amplitude. As the comparison between FIGS. 5 and 12 represents, the case illustrated in FIG. 12 does not contain the fundamental wave component denoted by the arrow 56*a*, the third harmonic component denoted by an arrow 56*c*, and the fifth harmonic component denoted by an arrow 56*e*. For this reason, according to the ultrasound probe 1** according to the embodiment, it is possible to reduce the odd harmonic components.

The control circuitry 16 controls the display 2 such that display 2 displays an ultrasound image based on the summing signal in which the odd harmonic components are reduced. In other words, the control circuitry 16 controls the display 2 such that the display 2 displays an ultrasound image based on the reflected-wave signal that is written in the capacitors 41_1 to **41_*n* of the analog delay circuit 22*b*_1 and the reflected-wave signal that is written in the capacitors 41_1 to 41_*n* of the analog delay circuit 22*b*_2**.

Figure 13:
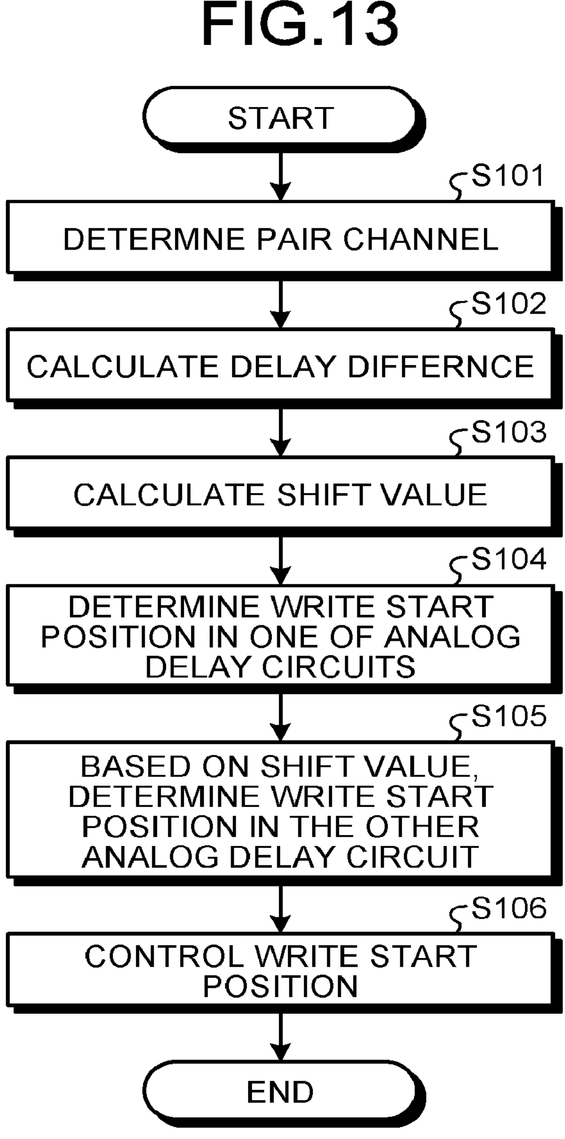
FIG. 13 is a flowchart illustrating an example of a flow of a process that is executed by the control circuit according to the embodiment.

An example of a flow of a process that is executed by the control circuitry 23 according to the embodiment will be described. FIG. 13 is a flowchart illustrating an example of a flow of a process that is executed by the control circuitry 23 according to the embodiment.

As illustrated in FIG. 13, the control circuitry 23 determines at least one pair channel from the channels in the same subarray (step S101). The control circuitry 23 calculates a delay difference between a reception delay corresponding to an analog delay circuit **22*b*_1 that is one of the two analog delay circuits 22*b*_contained in the pair channel and a reception delay corresponding to an analog delay circuit 22*b*_2 that is the other analog delay circuit 22*b*_(step S102). The analog delay circuit 22*b*_1 that is one of the analog delay circuits is the analog delay circuit 22*b* corresponding to one of the channels of the pair channel. The analog delay circuit 22*b*_2 that is the other analog delay circuit is the analog delay circuit 22*b***_corresponding to the other channel of the pair channel.

The control circuitry 23 adds the delay difference to the number of the capacitors SC corresponding to the half period (T1/2) of the noise period T1, thereby calculating a shift value (step S103).

The control circuitry 23 then determines a write start position in the analog delay circuit **22*b*_1 (step S104). The control circuitry 23 determines, as a write start position in the analog delay circuit 22*b*_2, the switched capacitor SC of the analog delay circuit 22*b*_2 that is shifted from the write start position in the analog delay circuit 22*b*_1 by the shift value that is calculated at step S103 (step S105**).

At step S106, the control circuitry 23 controls the write positions such that the write start position in the analog delay circuit **22*b*_1 is the write start position that is determined at step S104. At step S106, the control circuitry 23 controls the write start positions such that the write start position in the analog delay circuit 22*b*_2 is the write start position that is determined at step S105. The control circuitry 23 then ends the process illustrated in FIG. 13**.

The ultrasound probe 1 and the ultrasound diagnostic apparatus 100 according to the embodiment have been described. According to the ultrasound probe 1 and the ultrasound diagnostic apparatus 100 according to the embodiment, as described above, it is possible to reduce noise contained in a summing signal while inhibiting the frame rate from lowering.

Modification 1

In the embodiment, as described with reference to FIG. 12, the odd harmonic components are reduced; however, as illustrated in FIG. 12, the even harmonic components (the second harmonic component, the fourth harmonic component, and the sixth harmonic component) are not reduced and remain.

Figure 14:
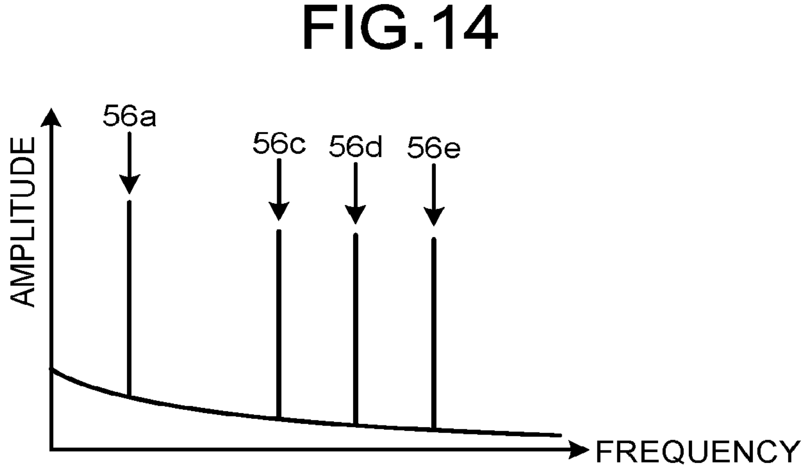
FIG. 14 is a diagram illustrating an example of noise that is contained in a summing signal in the case where read position in the analog delay circuit corresponding to one of channels and read position in the analog delay circuit corresponding to the other channel are shifted from each other by a ¼ period of a noise period.

The control circuitry 23 is able to reduce the second harmonic component and the sixth harmonic component by shifting the read position in the analog delay circuit **22*b* corresponding to one of the channels of the pair channel and the read position in the analog delay circuit 22*b* corresponding to the other channel from each other by a ¼ period (T1/4) of the noise period T1. In this case, however, as illustrated in FIG. 14, harmonic components other than the second harmonic component and the sixth harmonic component remain. FIG. 14 is a diagram illustrating an example of noise contained in a summing signal in the case where the read position in the analog delay circuit 22*b*_corresponding to one of the channels and the read position in the analog delay circuit 22*b***_corresponding to the other channel are shifted from each other by the ¼ period of the noise period T1.

The control circuitry 23 is capable of reducing the fourth harmonic component by shifting the read position in the analog delay circuit **22*b*_corresponding to one of the channels and the read position in the analog delay circuit 22*b***_corresponding to the other channel from each other by a ⅛ period (T1/8) of the noise period T1. In this case, however, harmonic components other than the fourth harmonic components remain.

A modification in which the ultrasound probe 1 reduces odd harmonic components and even harmonic components will be described as Modification 1. In the description of Modification 1, the same reference numbers as those of the embodiment are assigned to the same configuration as that of the embodiment and description thereof is sometimes omitted. In the description of Modification 1, aspects different from those of the embodiment will be mainly described and description of the same configuration is sometimes omitted.

Figure 15:
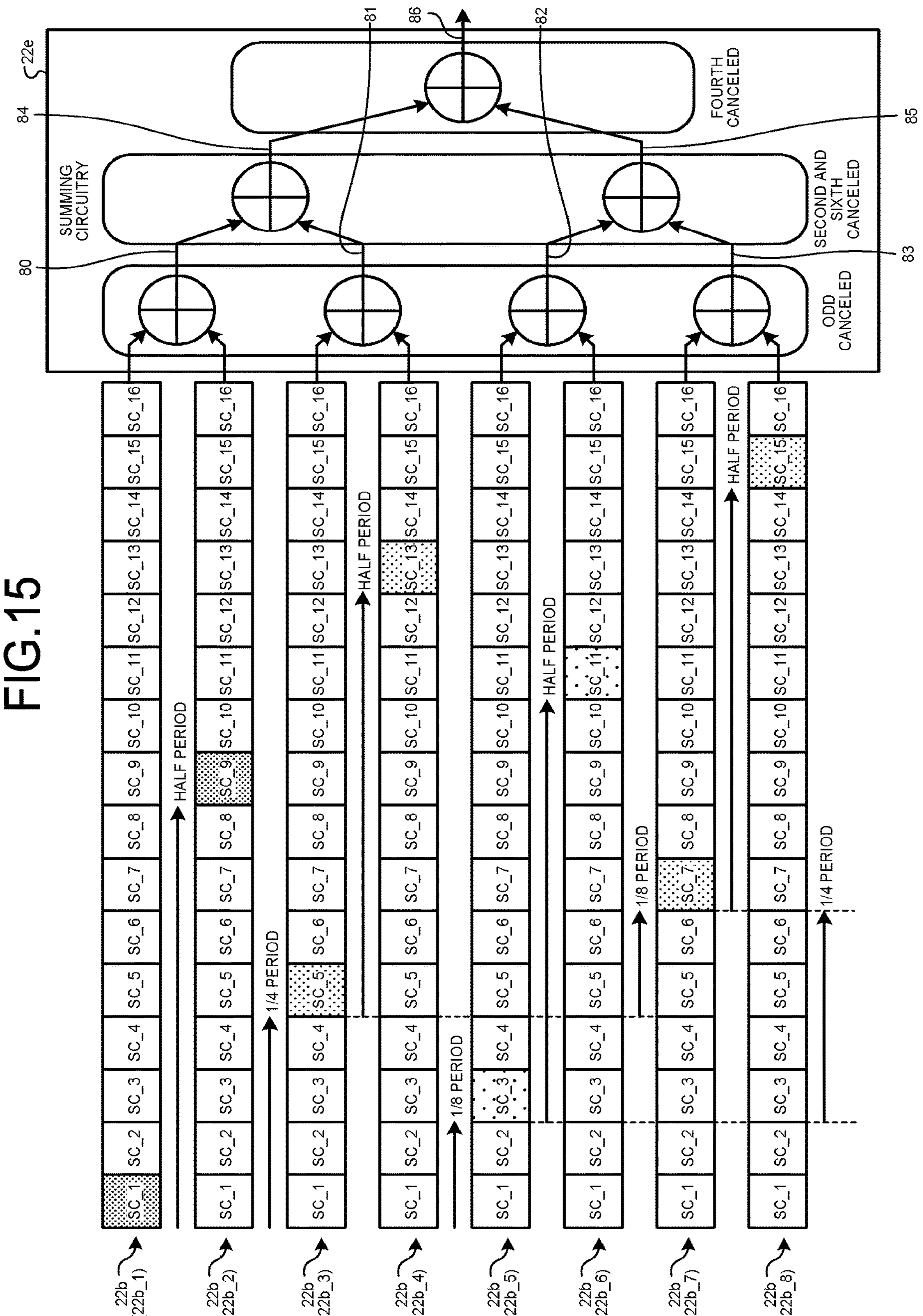
FIG. 15 is a diagram for describing an example of operations of an ultrasound probe according to Modification 1.

With reference to FIG. 15, an example of a method of controlling write start positions will be described. FIG. 15 is a diagram for describing an example of operations of the ultrasound probe 1 according to Modification 1. For example, in Modification 1, the control circuitry 23 does not determine a pair channel but determines a combination of any eight channels of the channels in the same subarray as a group channel.

For example, the control circuitry 23 determines, as a group channel, a combination of eight channels corresponding to eight analog delay circuits 22*b*_illustrated in FIG. 15. The analog delay circuits 22*b*_illustrated in FIG. 15 includes, for example, 16 switched capacitors SC_1 to SC_16. When the eight analog delay circuits 22*b* are described distinguishably from one another, the eight analog delay circuits 22*b* are denoted by analog delay circuits 22*b*_1 to 22*b*_8, respectively.

The control circuitry 23 controls the write start positions in the eight analog delay circuits 22*b* corresponding respectively to the eight channels that belong to the group channel such that the following three conditions from (Condition 1) to (Condition 3) are satisfied.

(Condition 1) Among the eight analog delay circuits 22*b*, there are four pairs of two analog delay circuits 22*b*_in which a difference between read positions at identical times is a difference corresponding to the half period (180 degrees) of the noise period T1.

(Condition 2) Among the eight analog delay circuits 22*b*, there are four pairs of two analog delay circuits 22*b*_in which a difference between read positions at identical times is a difference corresponding to the ¼ period (90 degrees) of the noise period T1.

(Condition 3) Among the eight analog delay circuits 22*b*, there are four pairs of two analog delay circuits 22*b*_in which a difference between read positions at identical times is a difference corresponding to the ⅛ period (45 degrees) of the noise period T1.

First of all, the case where the control circuitry 23 controls the write start positions such that Condition 1 described above is satisfied will be described. For example, the control circuitry 23 controls the write start position in the analog delay circuit 22*b*_1 and the write start position in the analog delay circuit 22*b*_2 such that the difference between the read position in the analog delay circuit 22*b*_1 and the read position in the analog delay circuit 22*b*_2 is a difference corresponding to the half period of the noise period T1. Under such control, in the case illustrated in FIG. 15, the difference between the read position (the switched capacitor SC_1) in the analog delay circuit 22*b*_1 and the read position (the switched capacitor SC_9) in the analog delay circuit 22*b*_2 is a difference corresponding to the half period of the noise period T1 (eight switched capacitors SC).

The control circuitry 23 controls the write start position in the analog delay circuit 22*b*_3 and the write start position in the analog delay circuit 22*b*_4 such that the difference between the read position in the analog delay circuit 22*b*_3 and the read position in the analog delay circuit 22*b*_4 is a difference corresponding to the half period of the noise period T1. Under such control, for example, in the case illustrated in FIG. 15, the difference between the read position in the analog delay circuit 22*b*_3 (the switched capacitor SC_5) and the read position in the analog delay circuit 22*b*_4 (the switched capacitor SC_13) is a difference corresponding to the half period of the noise period T1.

The control circuitry 23 controls the write start position in the analog delay circuit 22*b*_5 and the write start position in the analog delay circuit 22*b*_6 such that the difference between the read position in the analog delay circuit 22*b*_5 and the read position in the analog delay circuit 22*b*_6 is a difference corresponding to the half period of the noise period T1. Under such control, for example, in the case illustrated in FIG. 15, the difference between the read position in the analog delay circuit 22*b*_5 (the switched capacitor SC_3) and the read position in the analog delay circuit 22*b*_6 (the switched capacitor SC_11) is a difference corresponding to the half period of the noise period T1.

The control circuitry 23 controls the write start position in the analog delay circuit 22*b*_7 and the write start position in the analog delay circuit 22*b*_8 such that the difference between the read position in the analog delay circuit 22*b*_7 and the read position in the analog delay circuit 22*b*_8 is a difference corresponding to the half period of the noise period T1. Under such control, for example, in the case illustrated in FIG. 15, the difference between the read position in the analog delay circuit 22*b*_7 (the switched capacitor SC_7) and the read position in the analog delay circuit 22*b*_8 (the switched capacitor SC_15) is a difference corresponding to the half period of the noise period T1.

In Modification 1, when calculating a shift value in the case where the write start positions are controlled such that Condition 1 is satisfied, the control circuitry 23 uses "a number that is half of the number of all the switched capacitors SC that are used in one analog delay circuit 22*b*" as in the above-described embodiment. In Modification 1, the control circuitry 23 controls the write start positions of the two analog delay circuits 22*b*_such that Condition 1 is satisfied in the same manner as that in the above-described embodiment using the calculated shift value.

The case where the control circuitry 23 controls the write start positions such that Condition 2 described above is satisfied will be described. For example, the control circuitry 23 controls the write start position in the analog delay circuit 22*b*_1 and the write start position in the analog delay circuit 22*b*_3 such that the difference between the read position in the analog delay circuit 22*b*_1 and the read position in the analog delay circuit 22*b*_3 is a difference corresponding to the ¼ period of the noise period T1. Under such control, for example, in the case illustrated in FIG. 15, the difference between the read position (the switched capacitor SC_1) in the analog delay circuit 22*b*_1 and the read position (the switched capacitor SC_5) in the analog delay circuit 22*b*_3 is a difference corresponding to the ¼ period of the noise period T1 (four switched capacitors SC).

In modification 1, when calculating a shift value in the case where the write start positions are controlled such that Condition 2 is satisfied, the control circuitry 23 uses not "the number that is half of the number of all the switched capacitors SC that are used in one analog delay circuit 22*b*" but "a number obtained by multiplying the number of all the switched capacitors SC that are used in one analog delay circuit 22*b* by "¼"".

For example, as illustrated in FIG. 15, in the case where the number of all the switched capacitors used in one analog delay circuit 22*b* is "16", when calculating a shift value, the control circuitry 23 uses the number "4" obtained by multiplying "16" that is the number of the switched capacitors SC by "¼". In Modification 1, using the calculated shift value, the control circuitry 23 controls the write start positions in the two analog delay circuits 22*b* such that Condition 2 is satisfied in the same manner as that in the above-described embodiment.

The control circuitry 23 controls the write start position in the analog delay circuit 22*b*_2 and the write start position in the analog delay circuit 22*b*_4 such that the difference between the read position in the analog delay circuit 22*b*_2 and the read position in the analog delay circuit 22*b*_4 is a difference corresponding to the ¼ period of the noise period T1. Under such control, for example, in the case illustrated in FIG. 15, the difference between the read position in the analog delay circuit 22*b*_2 (the switched capacitor SC_9) and the read position in the analog delay circuit 22*b*_4 (the switched capacitor SC_13) is a difference corresponding to the ¼ period of the noise period T1.

The control circuitry 23 controls the write start position in the analog delay circuit 22*b*_5 and the write start position in the analog delay circuit 22*b*_7 such that the difference between the read position in the analog delay circuit 22*b*_5 and the read position in the analog delay circuit 22*b*_7 is a difference corresponding to the ¼ period of the noise period T1. Under such control, for example, in the case illustrated in FIG. 15, the difference between the read position in the analog delay circuit 22*b*_5 (the switched capacitor SC_3) and the read position in the analog delay circuit 22*b*_7 (the switched capacitor SC_7) is a difference corresponding to the ¼ period of the noise period T1.

The control circuitry 23 controls the write start position in the analog delay circuit 22*b*_6 and the write start position in the analog delay circuit 22*b*_8 such that the difference between the read position in the analog delay circuit 22*b*_6 and the read position in the analog delay circuit 22*b*_8 is a difference corresponding to the ¼ period of the noise period T1. Under such control, for example, in the case illustrated in FIG. 15, the difference between the read position in the analog delay circuit 22*b*_6 (the switched capacitor SC_11) and the read position in the analog delay circuit 22*b*_8 (the switched capacitor SC_15) is a difference corresponding to the ¼ period of the noise period T1.

The case where the control circuitry 23 controls the write start positions such that Condition 3 described above is satisfied will be described. For example, the control circuitry 23 controls the write start position in the analog delay circuit 22*b*_1 and the write start position in the analog delay circuit 22*b*_5 such that the difference between the read position in the analog delay circuit 22*b*_1 and the read position in the analog delay circuit 22*b*_5 is a difference corresponding to the ⅛ period of the noise period T1. Under such control, for example, in the case illustrated in FIG. 15, the difference between the read position (the switched capacitor SC_1) in the analog delay circuit 22*b*_1 and the read position (the switched capacitor SC_3) in the analog delay circuit 22*b*_5 is a difference corresponding to the ⅛ period of the noise period T1 (two switched capacitors SC).

In Modification 1, when calculating a shift value in the case where the write start positions are controlled such that Condition 3 is satisfied, the control circuitry 23 uses not "the number that is half of the number of all the switched capacitors SC that are used in one analog delay circuit 22*b*" but "a number obtained by multiplying the number of all the switched capacitors SC that are used in one analog delay circuit 22*b* by "⅛"".

For example, as illustrated in FIG. 15, in the case where the number of all the switched capacitors used in one analog delay circuit 22*b* is "16", when calculating a shift value, the control circuitry 23 uses the number "2" obtained by multiplying "16" that is the number of the switched capacitors SC by "⅛". In Modification 1, using the calculated shift value, the control circuitry 23 controls the write start positions in the two analog delay circuits 22*b* such that Condition 3 is satisfied in the same manner as that in the above-described embodiment.

The control circuitry 23 controls the write start position in the analog delay circuit 22*b*_2 and the write start position in the analog delay circuit 22*b*_6 such that the difference between the read position in the analog delay circuit 22*b*_2 and the read position in the analog delay circuit 22*b*_6 is a difference corresponding to the ⅛ period of the noise period T1. Under such control, for example, in the case illustrated in FIG. 15, the difference between the read position in the analog delay circuit 22*b*_2 (the switched capacitor SC_9) and the read position in the analog delay circuit 22*b*_6 (the switched capacitor SC_11) is a difference corresponding to the ⅛ period of the noise period T1.

The control circuitry 23 controls the write start position in the analog delay circuit 22*b*_3 and the write start position in the analog delay circuit 22*b*_7 such that the difference between the read position in the analog delay circuit 22*b*_3 and the read position in the analog delay circuit 22*b*_7 is a difference corresponding to the ⅛ period of the noise period T1. Under such control, for example, in the case illustrated in FIG. 15, the difference between the read position in the analog delay circuit 22*b*_3 (the switched capacitor SC_5) and the read position in the analog delay circuit 22*b*_7 (the switched capacitor SC_7) is a difference corresponding to the ⅛ period of the noise period T1.

The control circuitry 23 controls the write start position in the analog delay circuit 22*b*_4 and the write start position in the analog delay circuit 22*b*_8 such that the difference between the read position in the analog delay circuit 22*b*_4 and the read position in the analog delay circuit 22*b*_8 is a difference corresponding to the ⅛ period of the noise period T1. Under such control, for example, in the case illustrated in FIG. 15, the difference between the read position in the analog delay circuit 22*b*_4 (the switched capacitor SC_13) and the read position in the analog delay circuit 22*b*_8 (the switched capacitor SC_15) is a difference corresponding to the ⅛ period of the noise period T1.

In Modification 1, as illustrated in FIG. 15, the summing circuitry 22*e* adds the reflected-wave signal that is output from the analog delay circuit 22*b*_2 to the reflected-wave signal that is output from the analog delay circuit 22*b*_1, thereby generating a reflected-wave signal 80. Accordingly, the odd harmonic components that are superimposed onto the reflected-wave signal that is output from the analog delay circuit 22*b*_2 cancel the odd harmonic components that are superimposed onto the reflected-wave signal that is output from the analog delay circuit 22*b*_1.

The summing circuitry 22*e* adds the reflected-wave signal that is output from the analog delay circuit 22*b*_4 to the reflected-wave signal that is output from the analog delay circuit 22*b*_3, thereby generating a reflected-wave signal 81. Accordingly, the odd harmonic components that are superimposed onto the reflected-wave signal that is output from the analog delay circuit 22*b*_4 cancel the odd harmonic components that are superimposed onto the reflected-wave signal that is output from the analog delay circuit 22*b*_3.

The summing circuitry 22*e* adds the reflected-wave signal that is output from the analog delay circuit 22*b*_6 to the reflected-wave signal that is output from the analog delay circuit 22*b*_5, thereby generating a reflected-wave signal 82. Accordingly, the odd harmonic components that are superimposed onto the reflected-wave signal that is output from the analog delay circuit 22*b*_6 cancel the odd harmonic components that are superimposed onto the reflected-wave signal that is output from the analog delay circuit 22*b*_5.

The summing circuitry 22*e* adds the reflected-wave signal that is output from the analog delay circuit 22*b*_8 to the reflected-wave signal that is output from the analog delay circuit 22*b*_7, thereby generating a reflected-wave signal 83. Accordingly, the odd harmonic components that are superimposed onto the reflected-wave signal that is output from the analog delay circuit 22*b*_8 cancel the odd harmonic components that are superimposed onto the reflected-wave signal that is output from the analog delay circuit 22*b*_7.

The summing circuitry 22*e* adds the reflected-wave signal 81 to the reflected-wave signal 80, thereby generating a reflected-wave signal 84. Accordingly, the second harmonic component and the sixth harmonic component that are superimposed onto the reflected-wave signal 81 cancel the second harmonic component and the sixth harmonic component that are superimposed onto the reflected-wave signal 80.

The summing circuitry 22*e* adds the reflected-wave signal 83 to the reflected-wave signal 82, thereby generating a reflected-wave signal 85. Accordingly, the second harmonic component and the sixth harmonic component that are superimposed onto the reflected-wave signal 83 cancel the second harmonic component and the sixth harmonic component that are superimposed onto the reflected-wave signal 82.

The summing circuitry 22*e* adds the reflected-wave signal 85 to the reflected-wave signal 84, thereby generating a summing signal 86. Accordingly, the fourth harmonic component that is superimposed onto the reflected-wave signal 85 cancels the fourth harmonic component that is superimposed onto the reflected-wave signal 84. The summing circuitry 22*e* then transmits, to the transmitter-receiver circuitry 11 of the apparatus main unit 10, the summing signal 86 in which the odd harmonic components, the second harmonic component, the fourth harmonic component, and the sixth harmonic component are reduced.

The order in which the summing circuitry 22*e* sums reflected-wave signals that is described with reference to FIG. 15 is an example only. Even when the summing circuitry 22*e* sums multiple reflected-wave signals in another order of summation, the resultant summing signal is a signal in which the odd harmonic components, the second harmonic component, the fourth harmonic component, and the sixth harmonic component are reduced.

The ultrasound probe 1 and the ultrasound diagnostic apparatus 100 according to Modification 1 have been described. According to the ultrasound probe 1 and the ultrasound diagnostic apparatus 100 according to Modification 1, as in the embodiment, it is possible to reduce noise contained in a summing signal while inhibiting the frame rate from lowering. Furthermore, according to the ultrasound probe 1 and the ultrasound diagnostic apparatus 100 according to Modification 1, it is possible to reduce the second harmonic component, the fourth harmonic component, and the sixth harmonic component in addition to the odd harmonic components.

The ultrasound probe 1 according to Modification 1 is capable of reducing the noise components from the fundamental wave component to the seventh harmonic component. For example, when the fundamental frequency is around 1 MHz, the ultrasound probe 1 according to Modification 1 reduces noise components within a range from 1 MHz to 7 MHz. Thus, when an ultrasound probe with a frequency band within a range from 1 MHz to 7 MHz is used as the ultrasound probe 1 according to Modification 1, it is possible to obtain a summing signal in which noise components are particularly reduced. For example, a cardiovascular probe, or the like, is exemplified as such an ultrasound probe.

Modification 2

In the embodiment and Modification 1 described above, the case in which the number of the switched capacitors SC that are used is the same between the channels in the same subarray; however, the number of the switched capacitors SC may be different between the channels in the same subarray. Such a modification will be described as Modification 2. In the description of Modification 2, the same reference numbers as those of the embodiment and Modification 1 are assigned to the same configuration as that of the embodiment and Modification 1 and description thereof is sometimes omitted. In the description of Modification 2, aspects different from those of the embodiment and Modification 1 will be mainly described and description of the same configuration as those of the embodiment and Modification 1 is sometimes omitted.

For example, in Modification 2, based on a reception delay unique to each channel, the control circuitry 23 determines the number of switched capacitors SC that are used in the analog delay circuit 22*b*_corresponding to each channel (used switched capacitor number).

For example, as described above, when a reception delay that is represented by the number of system clocks is "r", based on the reception delay "r", the control circuitry 23 determines "r+2" as the number of the switched capacitors used.

In this case, the control circuitry 23 may determine, as the number of switched capacitors used in the analog delay circuit 22*b*, a value within a range between "r+2" and a maximum number M of switched capacitor SC usable in the analog delay circuit 22*b*, inclusive.

The case where delay processing to assign reception delays to a reflected-wave signal using the maximum number M of switched capacitors SC will be described. In this case, the period of the timing when part of the reflected-wave signal is written in an identical switched capacitor SC and the period of the timing when the part of the reflected-wave signal is read from the identical switched capacitor are both the above-described period T1.

In the following description, the period of the timing when part of the reflected-wave signal is written in the identical switched capacitor SC and the period of the timing when the part of the reflected-wave signal is read from the identical switched capacitor SC are referred to as a "control period".

In Modification 2, based on the period T1 and the determined used switched capacitor number, the control circuitry 23 calculates, for each channel, a control period in the case where switched capacitors SC corresponding to the used switched capacitor number are used. For example, the control circuitry 23 calculates a control period according to Equation (1) below.

$$TS=(U/M)\times T1 \quad (1)$$

In Equation (1), "TS" denotes the control period. "U" denotes the used switched capacitor number. "M" denotes the maximum number M of switched capacitors SC usable in the analog delay circuit 22*b*. "T1" denotes the period T1.

The control circuitry 23 calculates a control period for each channel. When used switched capacitor number is smaller than the maximum number M of switched capacitors SC that are usable, the control circuitry 23 calculates a control period shorter than the period T1.

The control circuitry 23 performs, on each channel, various types of control based on the determined used switched capacitor number and the calculated control period. For example, the control circuitry 23 generates, for each channel, a write control signal in which the state in which on is represented is repeated according to the control period. The control circuitry 23 generates, for each channel, a read control signal in which the state in which on is represented is repeated according to the control period. The control circuitry 23 transmits the write control signals and the read control signals to the switched capacitors SC corresponding to the used switched capacitor number, thereby causing the switched capacitors corresponding to the used switched capacitor number to execute the delay processing.

Based on the control period and the frequency band of the ultrasound probe 1, the control circuitry 23 specifies, for each channel, a fundamental wave component and harmonic components that are contained in the frequency band. Information representing the frequency band of the ultrasound probe 1 is previously stored in the storage circuitry 15 of the apparatus main unit 10. By issuing a request for information representing the frequency band to the apparatus main unit 10, the control circuitry 23 acquires the information representing the frequency band from the apparatus main unit 10. Using the control period and the frequency band that is represented by the acquired information, the control circuitry 23 specifies the fundamental wave component and the harmonic components that are contained in the frequency band.

Based on the fundamental wave component and the harmonic components that are specified, the control circuitry 23 determines a method of controlling write start positions by which the fundamental wave component and the harmonic components that are contained in the frequency band are reduced. The control circuitry 23 executes the determined method of controlling write start positions.

Figure 16:
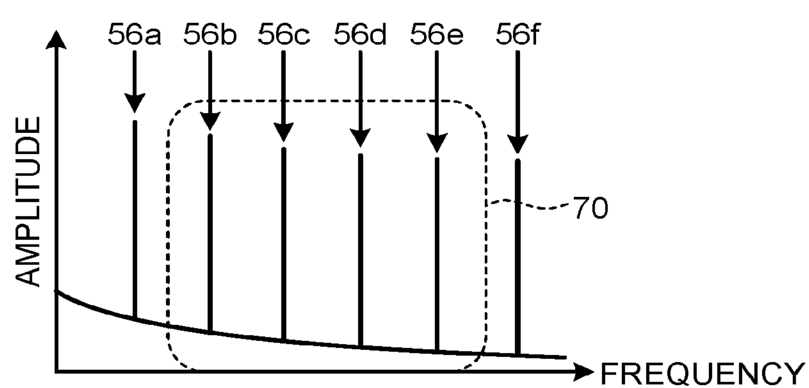
FIG. 16 is a diagram for describing an example of processing that is executed by the ultrasound probe according to Modification 2.

With reference to FIGS. 16 to 19, an example of a process that is executed by the ultrasound probe 1 will be described. FIGS. 16 to 19 are diagrams for describing the example of the process that is executed by the ultrasound probe 1 according to Modification 2. FIG. 16 illustrates an example of a relationship between a frequency band 70 of the ultrasound probe 1 and the fundamental wave component and the harmonic components in the case where the control period and the period T1 coincide.

As illustrated in FIG. 16, based on the control period and the frequency band 70 of the ultrasound probe 1, the control circuitry 23 specifies harmonic components from the second harmonic component to the fifth harmonic component that are contained in the frequency band 70. When harmonic components from the second harmonic component to the fifth harmonic component are specified, the control circuitry 23 determines a method of controlling write start positions that is described with reference to FIG. 15 as a method of controlling write start positions by which the specified harmonic components are reduced. The control circuitry 23 then executes the determined method of controlling write start positions.

Figure 17:
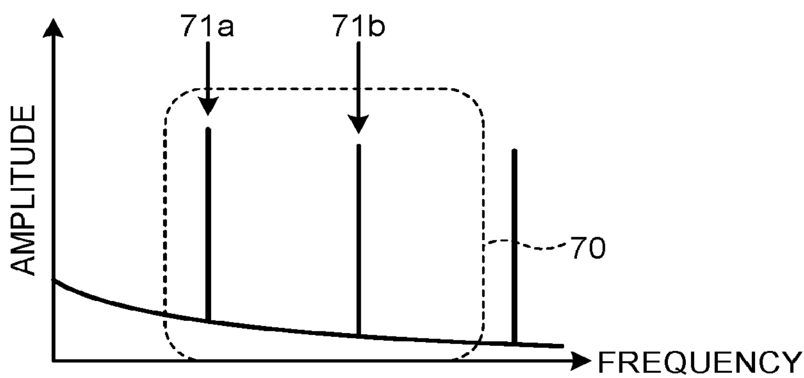
FIG. 17 is a diagram for describing an example of processing that is executed by the ultrasound probe according to Modification 2.

FIG. 17 illustrates an example of a relationship between the frequency band 70 of the ultrasound probe 1 and the fundamental wave component and the harmonic components in the case where the control period is the half period of the period T1.

As illustrated in FIG. 17, the component of the fundamental frequency (1/control period) represented by an arrow 71*a* contains a noise component. The component of twice the fundamental frequency (2/the control period) denoted by an arrow 71*b*_also contains a noise component.

Figure 18:
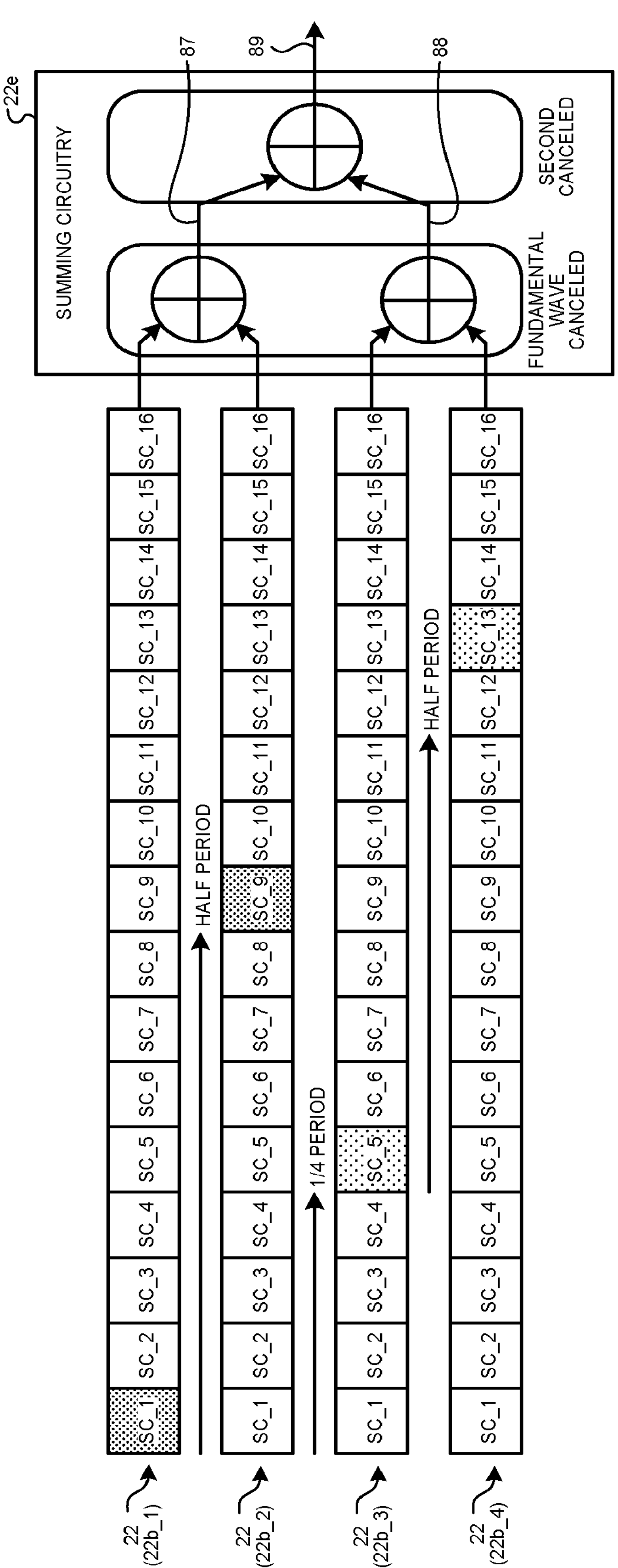
FIG. 18 is a diagram for describing an example of processing that is executed by the ultrasound probe according to Modification 2.

Based on the control period and the frequency band 70 of the ultrasound probe 1, as illustrated in FIG. 17, the control circuitry 23 specifies the fundamental wave component and the second harmonic component. FIG. 18 is a diagram illustrating an example of a method of controlling write start positions in the case where the fundamental wave component and the second harmonic component are specified. When the fundamental wave component and the second harmonic component are specified, the control circuitry 23 determines the method of controlling write start positions illustrated in FIG. 18 as the method of controlling write start positions by which the fundamental wave component and the second harmonic component that are specified are reduced. The control circuitry 23 then executes the determined method of controlling write start positions.

The method of controlling write start positions illustrated in FIG. 18 will be described. For example, the control circuitry 23 determines, as a group channel, a combination of any four channels of the channels in the same subarray. Specifically, the control circuitry 23 determines, as a group channel, a combination of four channels corresponding to the four analog delay circuits 22*b* illustrated in FIG. 18.

The analog delay circuit 22*b*_illustrated in FIG. 18 includes 32 switched capacitors SC; however, the used switched capacitor number is "16" and 16 switched capacitors SC_1 to SC_16 are used. When the four analog delay circuits 22*b* are described distinguishably, the four analog delay circuits 22*b* are denoted respectively as analog delay circuits 22*b*_1 to 22*b*_4.

The analog delay circuit 22*b*_1 illustrated in FIG. 18 delays a reflected-wave signal in a channel corresponding to the analog delay circuit 22*b*_1 using a plurality of capacitors 41_1 to 41_16 (not illustrated in FIG. 18). The analog delay circuit 22*b*_1 is an example of the first delay circuit. The channel corresponding to the analog delay circuit 22*b*_1 is an example of the first channel. A write start position in which writing the reflected-wave signal in one of the capacitors 41_1 to 41_16 of the analog delay circuit 22*b*_1 is started is an example of the first write start position. A read position in which the reflected-wave signal is read from one of the capacitors 41_1 to 41_16 of the analog delay circuit 22*b*_1 is an example of the first read position.

The analog delay circuit 22*b*_2 delays a reflected-wave signal in a channel corresponding to the analog delay circuit 22*b*_2 using a plurality of capacitors 41_1 to 41_16 (not illustrated in the drawings). The analog delay circuit 22*b*_2 is an example of the second delay circuit. The channel corresponding to the analog delay circuit 22*b*_1 is an example of the second channel. A write start position in which writing the reflected-wave signal in one of the capacitors 41_1 to 41_16 of the analog delay circuit 22*b*_2 is started is an example of the second write start position. A read position in which the reflected-wave signal is read from one of the capacitors 41_1 to 41_16 of the analog delay circuit 22*b*_2 is an example of the second read position.

The analog delay circuit 22*b*_3 delays a reflected-wave signal in a channel corresponding to the analog delay circuit 22*b*_3 using the capacitors 41_1 to 41_16 (not illustrated in the drawings). The analog delay circuit 22*b*_3 is an example of a third delay circuit. The channel corresponding to the analog delay circuit 22*b*_3 is an example of a third channel. A write start position in which writing the reflected-wave signal in one of the capacitors 41_1 to 41_16 of the analog delay circuit 22*b*_3 is started is an example of a third write start position. A read position in which the reflected-wave signal is read from one of the capacitors 41_1 to 41_16 of the analog delay circuit 22*b*_3 is an example of a third read position.

The analog delay circuit 22*b*_4 delays a reflected-wave signal in a channel corresponding to the analog delay circuit 22*b*_4 using the capacitors 41_1 to 41_16 (not illustrated in the drawings). The analog delay circuit 22*b*_4 is an example of a fourth delay circuit. The channel corresponding to the analog delay circuit 22*b*_4 is an example of a fourth channel. A write start position in which writing the reflected-wave signal in one of the capacitors 41_1 to 41_16 of the analog delay circuit 22*b*_4 is started is an example of a fourth write start position. A read position in which the reflected-wave signal is read from one of the capacitors 41_1 to 41_16 of the analog delay circuit 22*b*_4 is an example of a fourth read position.

The control circuitry 23 controls the write start positions in the four analog delay circuits 22*b*_corresponding to the four channels that belong to the group channel such that the following two conditions of (Condition 4) and (Condition 5) are satisfied.

(Condition 4) Among the four analog delay circuits 22*b*, there are two pairs of two analog delay circuits 22*b*_in which a difference between read positions at identical times is a difference corresponding to the half period (180 degrees) of the noise period T1 (the control period).

(Condition 5) Among the four analog delay circuits 22*b*, there are four pairs of two analog delay circuits 22*b*_in which a difference between read positions at identical times is a difference corresponding to the ¼ period (90 degrees) of the noise period T1 (the control period).

First of all, the case where the control circuitry 23 controls the write start positions such that Condition 4 described above is satisfied will be described. For example, the control circuitry 23 controls the write start position in the analog delay circuit 22*b*_1 and the write start position in the analog delay circuit 22*b*_2 such that the difference between the read position in the analog delay circuit 22*b*_1 and the read position in the analog delay circuit 22*b*_2 is a difference corresponding to the half period of the control period. Under such control, for example, in the case illustrated in FIG. 18, the difference between the read position (the switched capacitor SC_1) in the analog delay circuit 22*b*_1 and the read position (the switched capacitor SC_9) in the analog delay circuit 22*b*_2 is a difference corresponding to the half period of the control period (eight switched capacitors SC).

The control circuitry 23 controls the write start position in the analog delay circuit 22*b*_3 and the write start position in the analog delay circuit 22*b*_4 such that the difference between the read position in the analog delay circuit 22*b*_3 and the read position in the analog delay circuit 22*b*_4 is a difference corresponding to the half period of the control period. Under such control, for example, in the case illustrated in FIG. 18, the difference between the read position in the analog delay circuit 22*b*_3 (the switched capacitor SC_5) and the read position in the analog delay circuit 22*b*_4 (the switched capacitor SC_13) is a difference corresponding to the half period of the control period.

The case where the control circuitry 23 controls the write start positions such that Condition 5 described above is satisfied will be described. For example, the control circuitry 23 controls the write start position in the analog delay circuit 22*b*_1 and the write start position in the analog delay circuit 22*b*_3 such that the difference between the read position in the analog delay circuit 22*b*_1 and the read position in the analog delay circuit 22*b*_3 is a difference corresponding to the ¼ period of the control period. Under such control, for example, in the case illustrated in FIG. 18, the difference between the read position (the switched capacitor SC_1) in the analog delay circuit 22*b*_1 and the read position (the switched capacitor SC_5) in the analog delay circuit 22*b*_3 is a difference corresponding to the ¼ period of the control period (four switched capacitors SC).

The control circuitry 23 controls the write start position in the analog delay circuit 22*b*_2 and the write start position in the analog delay circuit 22*b*_4 such that the difference between the read position in the analog delay circuit 22*b*_2 and the read position in the analog delay circuit 22*b*_4 is a difference corresponding to the ¼ period of the control period. Under such control, for example, in the case illustrated in FIG. 18, the difference between the read position (the switched capacitor SC_9) in the analog delay circuit 22*b*_2 and the read position (the switched capacitor SC_13) in the analog delay circuit 22*b*_4 is a difference corresponding to the ¼ period of the control period.

In other words, the control circuitry 23 makes the read position in which the reflected-wave signal is read from one of the capacitors 41_1 to 41_16 of the analog delay circuit 22*b*_1, the read position in which the reflected-wave signal is read from one of the capacitors 41_1 to 41_16 of the analog delay circuit 22*b*_2, the read position in which the reflected-wave signal is read from one of the capacitors 41_1 to 41_16 of the analog delay circuit 22*b*_3, and the read position in which the reflected-wave signal is read from one of the capacitors 41_1 to 41_16 of the analog delay circuit 22*b*_4 at an identical time different from one another such that Condition 4 and Condition 5 are satisfied.

In Modification 2, as illustrated in FIG. 18, the summing circuitry 22*e* adds the reflected-wave signal that is output from the analog delay circuit 22*b*_2 to the reflected-wave signal that is output from the analog delay circuit 22*b*_1, thereby generating a reflected-wave signal 87. Accordingly, the fundamental wave component that is superimposed onto the reflected-wave signal that is output from the analog delay circuit 22*b*_2 cancels the fundamental wave component that is superimposed onto the reflected-wave signal that is output from the analog delay circuit 22*b*_1.

The summing circuitry 22*e*, for example, adds the reflected-wave signal that is output from the analog delay circuit 22*b*_4 to the reflected-wave signal that is output from the analog delay circuit 22*b*_3, thereby generating a reflected-wave signal 88. Accordingly, the fundamental wave component that is superimposed onto the reflected-wave signal that is output from the analog delay circuit 22*b*_4 cancels the fundamental wave component that is superimposed onto the reflected-wave signal that is output from the analog delay circuit 22*b*_3.

The summing circuitry 22*e*, for example, adds the reflected-wave signal 88 to the reflected-wave signal 87, thereby generating a summing signal 89. Accordingly, the second harmonic component that is superimposed onto the reflected-wave signal 88 cancels the second harmonic component that is superimposed onto the reflected-wave signal 87. The summing circuitry 22*e* transmits the summing signal 89 in which the fundamental wave component and the second harmonic component are reduced to the transmitter-receiver circuitry 11.

The order in which the summing circuitry 22*e* sums reflected-wave signals that is described with reference to FIG. 18 is an example only. Even when the summing circuitry 22*e* sums multiple reflected-wave signals in another order of summation, the resultant summing signal is a signal in which the fundamental wave component and the second harmonic component are reduced.

The summing circuitry 22*e* cancels the periodic noise, such as the fundamental wave component and the harmonic components, that is superimposed onto two reflected-wave signals by summing the two reflected-wave signals with a phase difference of 180 degrees in between. When the amplitudes of the periodic noise that is superimposed onto the two reflected-wave signals are approximately the same, the periodic noise is canceled appropriately. On the other hand, when the difference between the amplitudes of the periodic noises is large, the periodic noise is not canceled completely and thus remains. Thus, when the difference between the amplitudes of the periodic noise is large, it is preferable that the number of the fundamental wave component and harmonic components to be canceled be small. For this reason, as illustrated in FIG. 17, by using half of the period T1 as the control period, the control circuitry 23 shifts the fundamental wave component and the harmonic components to a side of high bandwidth and reduces the number of harmonic components within the frequency band 70 of the ultrasound probe 1 that are to be canceled.

Figure 19:
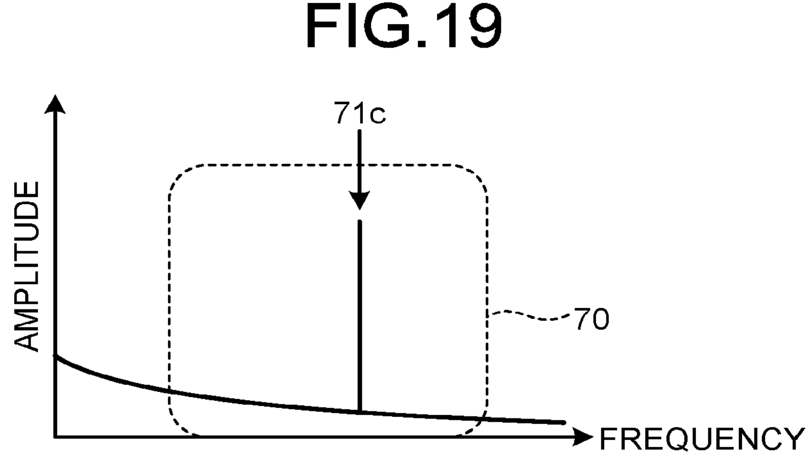
FIG. 19 is a diagram for describing an example of processing that is executed by the ultrasound probe according to Modification 2.

FIG. 19 illustrates the frequency band 70 of the ultrasound probe 1 in the case where the control period is the ¼ period of the period T1 and a relationship between the fundamental wave component and the harmonic components. As illustrated in FIG. 19, the component of the fundamental frequency (1/control period) represented by an arrow 71*c* contains a noise component.

Based on the control period and the frequency band 70 of the ultrasound probe 1, the control circuitry 23 specifies the fundamental wave component contained in the frequency band 70 as illustrated in FIG. 19. When the fundamental wave component is specified, the control circuitry 23 determines the method of controlling write start positions that is described with reference to FIGS. 10 and 11 as a method of controlling write start positions such that the fundamental wave component is reduced. The control circuitry 23 then executes the determined method of controlling write start positions.

As described with reference to FIGS. 16 to 19, in Modification 2, the control circuitry 23 performs control such that write positions in each of which a reflected-wave signal is written in a capacitor in, among the analog delay circuits 22*b*, analog delay circuits corresponding in number to the types of noise components contained in the frequency band 70 of the ultrasound probe 1 are different from each other. In Modification 2, the control circuitry 23 performs control such that read positions in each of which a reflected-wave signal is read from a capacitor in, among the analog delay circuits 22*b*, the analog delay circuits 22 corresponding in number to the types of noise components that are contained in the frequency band 70 of the ultrasound probe 1 are different from each other.

The ultrasound probe 1 and the ultrasound diagnostic apparatus 100 according to Modification 2 have been described. According to the ultrasound probe 1 and the ultrasound diagnostic apparatus 100 according to Modification 2, as in the embodiment and Modification 1, it is possible to reduce noise contained in a summing signal while inhibiting the frame rate from lowering. Furthermore, according to the ultrasound probe 1 and the ultrasound diagnostic apparatus 100 according to Modification 2, it is possible to reduce the volume of remaining noise.

In the above-described embodiment, Modification 1 and Modification 2, $2^N$ (N is 1, 2 or 3) analog delay circuits 22*b* that delay reflected-wave signals using a plurality of capacitors are paired or grouped and write start positions are controlled in each pair or in each group. The control circuitry 23 makes write start positions in each of which writing a reflected-wave signal in the capacitor of each of the $2^N$ analog delay circuits 22*b* is started different from each other such that there is, for each of the $2^N$ analog delay circuits 22*b*, another analog delay circuit 22*b*_that outputs a delayed ultrasound signal with a phase difference of $(360/2^t)$ degrees (t=1, . . . , N) with respect to the reflected-wave signal that is delayed by the analog delay circuit 22*b*. The summing circuitry 22*e* then sums the reflected-wave signals that are delayed respectively by the $2^N$ analog delay circuits 22*b*, thereby generating a summing signal. "N" may be a natural number other than 1 to 3 and equal to or larger than 4. In other words, "N" is preferably a natural number simply.

According to the ultrasound probe 1 and the ultrasound diagnostic apparatus 100 of at least one of the embodiments, it is possible to reduce noise that is superimposed onto a summing signal while inhibiting the frame rate from lowering.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An apparatus, comprising:

a first delay circuit that delays an ultrasound signal in a first channel using a first plurality of capacitors, the first delay circuit corresponding to the first channel;

a second delay circuit that delays an ultrasound signal in a second channel, which is different from the first channel, using a second plurality of capacitors, the second delay circuit corresponding to the second channel;

a third delay circuit that delays an ultrasound signal in a third channel using a third plurality of capacitors;

a fourth delay circuit that delays an ultrasound signal in a fourth channel using a fourth plurality of capacitors;

processing circuitry configured to make a first write start position in which writing the ultrasound signal in a capacitor in the first delay circuit is started and a second write start position in which writing the ultrasound signal in a capacitor in the second delay circuit is started different from each other by inputting a control signal which has a periodicity, to each of the first delay circuit and the second delay circuit; and summing circuitry configured to generate a summing signal by summing the ultrasound signal that is delayed by the first delay circuit and the ultrasound signal that is delayed by the second delay circuit, wherein the processing circuitry is further configured to make the first write start position and the second write start position different from each other such that a periodic noise resulting from the periodicity of the control signal and contained in the summing signal is smaller than a periodic noise resulting from the periodicity of the control signal and contained in the ultrasound signal that is delayed by the first delay circuit and in the ultrasound signal that is delayed by the second delay circuit, and wherein the processing circuitry is further configured to make the first write start position, the second write start position, a third write start position in which writing the ultrasound signal in a capacitor in the third delay circuit is started, and a fourth write start position in which writing the ultrasound signal in a capacitor in the fourth delay circuit is started different from one another such that a phase difference between the ultrasound signal that is delayed by the third delay circuit and the ultrasound signal that is delayed by the fourth delay circuit is 180 degrees and a phase difference between the ultrasound signal that is delayed by the first delay circuit and the ultrasound signal that is delayed by the third delay circuit and a phase difference between the ultrasound signal that is delayed by the second delay circuit and the ultrasound signal that is delayed by the fourth delay circuit are 90 degrees.

2. The apparatus according to claim 1, wherein the processing circuitry is further configured to make the first write start position and the second write start position different from each other based on a number of the first plurality of capacitors contained in the first delay circuit or a number of the second plurality of capacitors contained in the second delay circuit.

3. The apparatus according to claim 1, wherein the summing circuitry is further configured to generate an additional summing signal by summing (A) the summing signal generated by summing the ultrasound signal that is delayed by the first delay circuit and the ultrasound signal that is delayed by the second delay circuit, and (B) a signal generated by summing the ultrasound signal that is delayed by the third delay circuit and the ultrasound signal that is delayed by the fourth delay circuit.

4. The apparatus according to claim 1, wherein the first delay circuit periodically writes the ultrasound signal in the capacitor of the first delay circuit, and the second delay circuit periodically writes the ultrasound signal in the capacitor of the second delay circuit.

5. The apparatus according to claim 4, wherein the first delay circuit periodically reads the ultrasound signal from the capacitor of the first delay circuit, and the second delay circuit periodically reads the ultrasound signal from the capacitor of the second delay circuit.

6. The apparatus according to claim 1, wherein the first delay circuit periodically writes the ultrasound signal in the capacitor of the first delay circuit, the second delay circuit periodically writes the ultrasound signal in the capacitor of the second delay circuit, the third delay circuit periodically writes the ultrasound signal in the capacitor of the third delay circuit, and the fourth delay circuit periodically writes the ultrasound signal in the capacitor of the fourth delay circuit.

7. The apparatus according to claim 1, wherein a number of the first plurality of capacitors that are used by the first delay circuit and a number of the second plurality of capacitors that are used by the second delay circuit are equal to each other.

8. The apparatus according to claim 1, wherein the apparatus is an ultrasound probe.

9. The apparatus according to claim 1, wherein the apparatus is an ultrasound diagnostic apparatus.

10. The apparatus according to claim 1, wherein the processing circuitry is further configured to make a first read position in which the ultrasound signal is read at a first time from the capacitor of the first delay circuit and a second read position in which the ultrasound signal is read at a second time from the capacitor of the second delay circuit different from each other by making the first write start position and the second write start position different from each other, the first and second times being identical.

11. The apparatus according to claim 1, wherein the processing circuitry is further configured to make the first write start position and the second write start position different from each other based on a delay of the first delay circuit and a delay of the second delay circuit.

12. The apparatus according to claim 1, wherein the processing circuitry is further configured to make the first write start position, the second write start position, the third write start position, and the fourth write start position different from one another based on a delay of the first delay circuit, a delay of the second delay circuit, a delay of the third delay circuit, and a delay of the fourth delay circuit.

13. An apparatus, comprising:

a first delay circuit that delays an ultrasound signal in a first channel using a first plurality of capacitors, the first delay circuit corresponding to the first channel;

a second delay circuit that delays an ultrasound signal in a second channel, which is different from the first channel, using a second plurality of capacitors, the second delay circuit corresponding to the second channel;

processing circuitry configured to make a first write start position in which writing the ultrasound signal in a capacitor in the first delay circuit is started and a second write start position in which writing the ultrasound signal in a capacitor in the second delay circuit is started different from each other; and summing circuitry configured to generate a summing signal by summing the ultrasound signal that is delayed by the first delay circuit and the ultrasound signal that is delayed by the second delay circuit, wherein the processing circuitry is further configured to make the first write start position and the second write start position different from each other such that a noise contained in the summing signal is smaller than a noise contained in the ultrasound signal that is delayed by the first delay circuit and in the ultrasound signal that is delayed by the second delay circuit, wherein the apparatus further comprises a third delay circuit that delays an ultrasound signal in a third channel using a third plurality of capacitors; and a fourth delay circuit that delays an ultrasound signal in a fourth channel using a fourth plurality of capacitors; and wherein the processing circuitry is further configured to make the first write start position, the second write start position, a third write start position in which writing the ultrasound signal in a capacitor in the third delay circuit is started, and a fourth write start position in which writing the ultrasound signal in a capacitor in the fourth delay circuit is started different from one another such that a phase difference between the ultrasound signal that is delayed by the third delay circuit and the ultrasound signal that is delayed by the fourth delay circuit is 180 degrees and a phase difference between the ultrasound signal that is delayed by the first delay circuit and the ultrasound signal that is delayed by the third delay circuit and a phase difference between the ultrasound signal that is delayed by the second delay circuit and the ultrasound signal that is delayed by the fourth delay circuit are 90 degrees.

* * * * *